United States Patent
Jung et al.

(10) Patent No.: US 10,537,518 B2
(45) Date of Patent: Jan. 21, 2020

(54) HOMOGENIZATION SYSTEM OF DRUGS INTO BIODEGRADABLE POLYMER: SMART POLYMER SYSTEM

(71) Applicant: Juvic Inc., Seoul (KR)

(72) Inventors: Hyung Il Jung, Seoul (KR); Dangol Manita, Seoul (KR)

(73) Assignee: Juvic Inc., Seoul (KR)

( * ) Notice: Subject to any disclaimer, the term of this patent is extended or adjusted under 35 U.S.C. 154(b) by 32 days.

(21) Appl. No.: 15/105,465

(22) PCT Filed: Mar. 28, 2016

(86) PCT No.: PCT/KR2016/003164
§ 371 (c)(1),
(2) Date: Jun. 16, 2016

(87) PCT Pub. No.: WO2016/159620
PCT Pub. Date: Oct. 6, 2016

(65) Prior Publication Data
US 2017/0105928 A1 Apr. 20, 2017

(30) Foreign Application Priority Data
Mar. 27, 2015 (KR) .......................... 10-2015-0043416

(51) Int. Cl.
| A61K 9/00 | (2006.01) |
| A61K 9/50 | (2006.01) |
| A61K 31/165 | (2006.01) |
| A61M 37/00 | (2006.01) |
| A61K 9/14 | (2006.01) |
| A61K 9/51 | (2006.01) |

(52) U.S. Cl.
CPC .............. *A61K 9/0014* (2013.01); *A61K 9/50* (2013.01); *A61K 31/165* (2013.01)

(58) Field of Classification Search
None
See application file for complete search history.

(56) References Cited

U.S. PATENT DOCUMENTS

| 8,586,062 B2 * | 11/2013 | Khopade .............. A61K 9/1075 424/400 |
| 2006/0280797 A1 * | 12/2006 | Shoichet .............. A61K 9/0024 424/486 |
| 2010/0098735 A1 * | 4/2010 | Jain ...................... A61K 9/0024 424/422 |
| 2011/0177139 A1 * | 7/2011 | Jung .................... A61K 9/0021 424/400 |

FOREIGN PATENT DOCUMENTS

| JP | 10-0793615 B1 | 1/2008 |
| JP | 2010-82401 A | 4/2010 |
| JP | 2012-504160 A | 2/2012 |
| KR | 10-2009-0131540 A | 12/2009 |
| KR | 10-2010-0037389 A | 4/2010 |
| KR | 10-2011-0022554 A | 3/2011 |
| KR | 10-2014-0101903 A | 8/2014 |

OTHER PUBLICATIONS

Chen et al.; Biomacromolecules (2012) 13, pp. 4022-4031; published Dec. 10, 2012.*
Chu et al.; J. Controlled Release; vol. 149, Iss. 3; published Feb. 10, 2011, pp. 242-249.*
Box et al., "Using Measured $pK_a$, LogP and Solubility to Investigate Supersaturation and Predict BCS Class," *Current Drug Metabolism* 9:869-878, 2008.
Brand et al., "Collagen-induced arthritis," *Nature Protocols* 2(5):1269-1275, 2007.
Dick, "Solvent Neurotoxicity," *Occup Environ Med* 63:221-226, 2006.
Chadha et al., "Analytical techniques used to characterize drug-polyvinylpyrrolidone systems in solid and liquid states—An overview," *Journal of Scientific & Industrial Research* 65:459-469, 2006.
Funke et al., "In-vitro release and transdermal fluxes of a highly lipophilic drug and of enhancers from matrix TDS," *Journal of Controlled Release* 82:63-70, 2002.
Ito et al., "Effect of Lipophilicity on the Bioavailability of Drugs After Percutaneous Administration by Dissolving Microneedles," *Journal of Pharmaceutical Sciences* 101(3):1145-1156, 2012.
Kim et al., "Droplet-born air blowing: Novel dissolving microneedle fabrication," *Journal of Controlled Release* 170:430-436, 2013.
Kim et al., "Novel cosmetic patches for wrinkle improvement: retinyl retinoate- and ascorbic acid-loaded dissolving microneedles," *International Journal of Cosmetic Science* 36:207-212, 2014.
Lazar et al., "Kinetics of Penetration Influence the Apparent Potency of Vanilloids on TRPV1," *Molecular Pharmacology* 69:1166-1173, 2006.
Leeson et al., "The influence of drug-like concepts on decision-making in medicinal chemistry," *Nature Reviews Drug Discovery* 6:881-890, 2007.

(Continued)

*Primary Examiner* — Jeffrey T. Palenik
(74) *Attorney, Agent, or Firm* — Seed IP Law Group LLP

(57) ABSTRACT

A viscous composition for transdermal drug delivery, a method of preparing the same, and a microstructure device prepared using the viscous composition are provided. Here, the viscous composition includes colloidal particles formed of a combination of a drug and a biodegradable polymer, and the biodegradable polymer includes a first amphiphilic polymer. The use of a solvent can be minimized to homogenize the drug in the biodegradable polymer including the first amphiphilic polymer, thereby forming colloidal particles. Therefore, since a separate solvent cannot be used, the microstructure device is expected to be a transdermal drug delivery system which is safe, efficient or useful for drugs which do not include a proper solvent, show poor bioavailability or have a high molecular weight.

10 Claims, 19 Drawing Sheets

(56) References Cited

OTHER PUBLICATIONS

Lipinski, "Drug-like properties and the causes of poor solubility and poor permeability," *Journal of Pharmacological and Toxicological Methods* 44:235-249, 2000.

Liu et al., "Hydrogels in aqueous phases of polyvinylalcohol (PVA), surfactants and clay minerals," *Colloid Polym Sci* 283:24-32, 2004.

Ma et al., "Control of drug crystallization in transdermal matrix system," *International Journal of Pharmaceuticals* 142:115-119, 1996.

Manju et al., "Conjugation of curcumin onto hyaluronic acid enhances its aqueous solubility and stability," *Journal of Colloid and Interface Science* 359:318-325, 2011.

Park et al., "Capsaicin inhibits the production of tumor necrosis factor α by LPS-stimulated murine macrophages, RAW 264.7: a PPARγ ligand-like action as a novel mechanism," *FEBS Letters* 572:266-270, 2004.

Rautio et al., "Prodrugs: design and clinical applications," *Nature Reviews Drug Discovery* 7:255-270, 2008.

Sawant et al., "Drug release from hydrothanolic gels. Effect of drug's lipophilicy (log P), polymer-drug interactions and solvent lipophilicity," *International Journal of Pharmaceuticals* 396:45-52, 2010.

Schulz et al., "Influence of adsorbents in transdermal matrix patches on the release and the physical state of ethinyl estradiol and levonorgestrel," *European Journal of Pharmaceuticals and Biopharmaceuticals* 77:240-248, 2011.

Singhavi et al., "Improvement of dissolution behavior of poorly water soluble drugs by biodegradable polymeric submicron carriers containing sparingly methylated β-cyclodextrin," *J. Mater. Sci.: Mater. Med.* 24:941-949, 2013.

Tekade et al., "Investigation on Physical-Mechanical Properties of Natural Polymer Films," *International Journal of PharmTech Research* 2(1):106-112, 2010.

Tu et al., "Study on the Interaction Between Polyvinylpyrrolidone and Platinum Metals During the Formation of the Colloidal Metal Nanoparticles," *Chinese Journal of Polymer Science* 26(1):23-29, 2008.

Wadhwa et al., "Emulsion Forming Drug Delivery System for Lipophilic Drugs," *Acta Poloniae Pharmaceutica—Drug Research* 69(2):179-191, 2012.

Wang et al., "Quantitative Analysis of Molecular Absorption into PDMS Microfluidic Channels," *Annals of Biomedical Engineering* 40(9):1862-1873, 2012.

Whitehouse, "Tumour necrosis factor alpha inhibitors for the treatment of adult rheumatoid arthritis," *Australian Presciber* 28(1):5-7, 2005.

Dangol et al., "Innovative polymeric system (IPS) for solvent-free lipophilic drug transdermal delivery via dissolving microneedles," *Journal of Controlled Release* 223:118-125, 2016.

Lee et al., "Nanostructured lipid carrier-loaded hyaluronic acid microneedles for controlled dermal delivery of a lipophilic molecule," *International Journal of Nanomedicine* 9:289-299, 2014.

Sullivan, "Polymer Microneedles for Transdermal Delivery of Biopharmaceuticals," doctoral dissertation, Georgia Institute of Technology, Atlanta, GA, May 2009, 101 pages.

\* cited by examiner

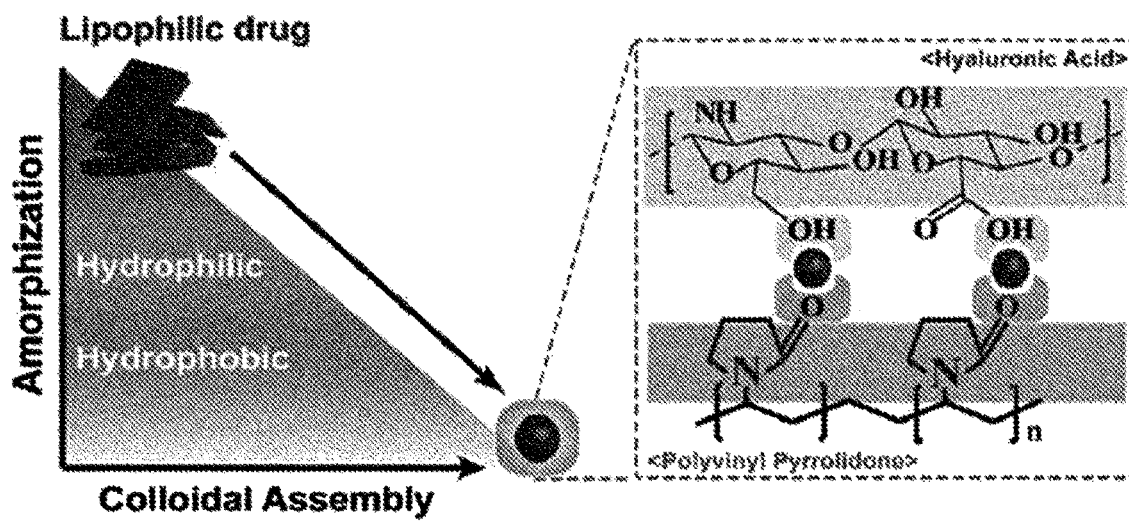
FIG. 1B
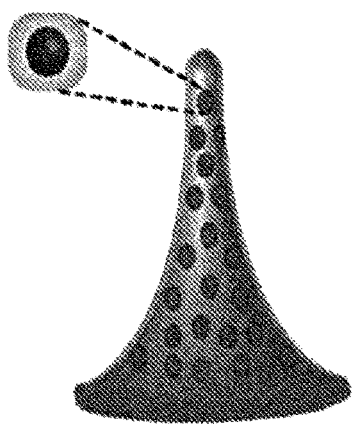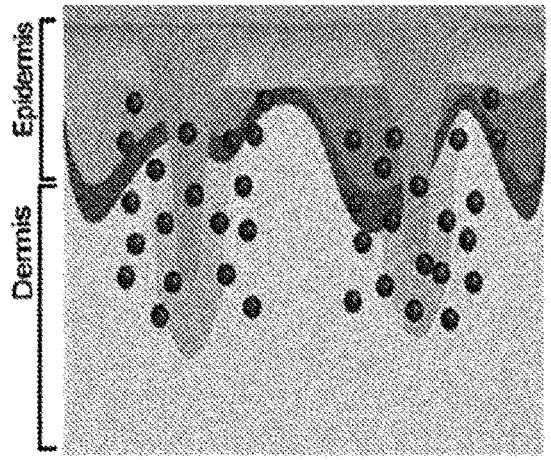
FIG. 1C

HOMOGENIZATION SYSTEM OF DRUGS INTO BIODEGRADABLE POLYMER: SMART POLYMER SYSTEM

TECHNICAL FIELD

The present invention relates to a homogenization system of drugs into a biodegradable polymer, that is, a smart polymer system.

BACKGROUND ART

Among drugs, lipophilic drugs show a high cure rate by enhancing the absorption and metabolism of drugs due to high permeability across cell lipid membranes (1). Therefore, great interest has been brought to the development of the drugs (2). However, to improve the bioavailability of the lipophilic drugs, the lipophilic drugs should first be dissolved in a proper solvent, and then used. 40% of the lipophilic drugs have not appeared in the pharmaceutical market due to the lack of proper solvents and drug delivery systems (3, 4). Using an organic solvent is the method most widely used to improve the solubility of such lipophilic drugs, but there are biological safety issues and various adverse side effects caused by the use of the organic solvent (5). Owing to these problems, a non-solvent drug delivery system (DDS) capable of safely delivering various types of lipophilic drugs without using a solvent is required.

The non-solvent delivery system refers to a system that can deliver a drug without using a solubilizing solvent for lipophilic drugs in the form of crude powder. The lipophilic drugs in the form of crude powder used so far may be transdermally delivered for surgical operation (8), or may be applied to nasal drug delivery using a high-pressure powder spray mechanism (9). Such a nasal drug delivery system cannot be used for general methods for lipophilic drug delivery since a dose of the drug cannot be easily adjusted through spraying (10), and airway hypersensitivity and infections are caused by repeated absorption of drugs through the nasal cavities (11). Oral lipophilic drug delivery has a probability of overcoming the limitations of the above-described nasal drug delivery, but the bioavailability of the drugs may be lowered since the drugs undergo first pass metabolism in the liver. Based on this situation, the transdermal drug delivery system is a useful drug delivery route for lipophilic drugs in the following aspects: (i) the dose of the drug may be easily adjusted (12), (ii) adverse reactions may be reduced (13), and (iii) a first pass metabolism effect may be avoided. However, it is very difficult to deliver a powder-type lipophilic drug through the skin barrier without solubilizing the lipophilic drug. For this reason, the present inventors have developed a smart polymer system (SPS) capable of dissolving a lipophilic drug in the form of crude powder in a biodegradable polymer without using a solubilizing solvent for the lipophilic drug, and have developed a transdermal drug delivery system capable of overcoming the skin barrier and thus delivering the powder-type lipophilic drug by manufacturing a biodegradable microneedle for the smart polymer system.

Since the drug delivery system of the present invention using a biodegradable polymer requires no solvent to dissolve a lipophilic drug, the drug delivery system may be widely used to deliver various lipophilic drugs without any limitation on the solvent, and may be used as a novel lipophilic drug delivery system capable of overcoming the limitations of the oral and nasal drug delivery using as a drug delivery mechanism a transdermal drug delivery system such as biodegradable microneedles configured to form cracks through a skin barrier and disperse a drug through layers of the skin.

Throughout this specification, a number of research papers and patent documents are cited and provided in parentheses. The disclosures of the cited research papers and patent documents are incorporated herein by reference in their entirety to more fully describe the state of the art to which the present invention pertains and the content of the present invention.

DISCLOSURE

Technical Problem

The present invention is directed to a viscous composition for transdermal drug delivery which includes colloidal particles formed of a combination of a drug and a biodegradable polymer. Here the biodegradable polymer includes a first amphiphilic polymer.

However, other objects and advantages of the present invention will be more clearly understood by the following detailed description, appended claims and accompanying drawings.

Technical Solution

Viscous Composition for Transdermal Drug Delivery

An aspect of the present invention is to provide a viscous composition for transdermal drug delivery which includes colloidal particles formed of a combination of a drug and a biodegradable polymer. Here the biodegradable polymer includes a first amphiphilic polymer.

The present inventors have exerted much effort in conducting intensive research to develop a safe and efficient method of transdermally delivering various drugs such as lipophilic drugs. As a result, the present inventors have first developed a method of homogenizing a powder-type drug using a "smart polymer system (SPS)" formed of a biodegradable polymer including an amphiphilic polymer (for example, a combination of hyaluronic acid (HA) and polyvinyl pyrrolidone (PVP)), and have confirmed that microneedles manufactured by applying this technique are used to transdermally deliver various drugs with high efficiency without using a separate soluble solvent regardless of the lipophilicity/water solubility and molecular weights of the drugs themselves. Homogenization of the powder-type drugs and a decrease in particle size of the powder-type drugs may be achieved by means of the SPS, and thus the microneedles for transdermal drug delivery may be uniformly mounted. Such a transdermal drug delivery system for powder-type drugs was first presented by the present inventors.

The transdermal delivery of conventional lipophilic drugs is limited due to high lipophilicity and molecular weight of the lipophilic drugs themselves. Also, types of microneedles for delivery of drugs using a hydrophilic polymer cannot be manufactured since it is impossible to homogenize the lipophilic drugs and the hydrophilic polymer. Considering these problems, the present inventors have prepared a "viscous composition for transdermal drug delivery" capable of permeating through the skin regardless of the lipophilicity/water solubility and molecular weights of the drugs using a biodegradable polymer including an amphiphilic polymer as a novel approach to deliver powder-type drugs. In the present invention, the colloidal particles including a powder-type drug are formed at a mixing ratio of the biodegradable polymer including the amphiphilic polymer (for example, hyaluronic acid and polyvinyl pyrrolidone). The "smart polymer system" using such a biodegradable polymer enables the formation of biodegradable microstructures (for example, microneedles). In the present invention, Nile Red is used for a powder-type lipophilic drug model. The microstructures of the present invention may deliver a medium lipophilic drug such as capsaicin for the treatment of rheumatoid arthritis.

Lipophilic drugs belong to a potential drug candidate group for drug discovery, but hardly appear in the pharmaceutical market due to the absence of a solubilizing solvent and a proper delivery technique. A transdermal drug delivery system (TDDS) has started to emerge for recent delivery of lipophilic drugs. Nevertheless, the use of TDDS for delivery of highly lipophilic drugs has still been limited due to the absence of biological safety, convenience and an effective strategy for pain-free delivery systems.

Accordingly, the present inventors have first developed a smart polymer system (SPS) as an alternative to apply a powder-type lipophilic drug to the transdermal drug delivery system. The smart polymer system of the present invention forms a nano-sized colloidal structure capable of being fabricated into biodegradable microneedles by homogenizing the lipophilic drug and the biodegradable polymer. For example, when the smart polymer system of the present invention is used, a powder of the lipophilic drug is phase-transitioned from a crystal form to an amorphous form due to an internal chemical bond between the lipophilic drug and the biodegradable polymer while homogenizing the lipophilic drug and the biodegradable polymer, thereby forming nano-sized colloidal particles.

In the present invention, the term "phase transition" refers to a state in which a lipophilic drug powder is changed from a crystal form to a semi-crystal form. Such a state may occur in a viscous composition for transdermal drug delivery when the viscous composition is prepared. However, the state may also occur under layers of the skin when the viscous composition is transdermally administered after the manufacture of microstructures.

The colloidal structure enables the release of the lipophilic drug powder into a layer of the skin in the form of a powder for TDDS. The transdermal delivery of powder-type lipophilic drugs, for example, Nile Red and capsaicin, is achieved by uniformly loading the powder-type lipophilic drugs onto the biodegradable microneedles using the SPS. The microneedles manufactured to mount capsaicin using the SPS of the present invention have an improved therapeutic effect of capsaicin on antigen-induced arthritis in a DBA/1 mouse model, compared to a solvent-based topical formulation, indicating that the drug delivery system of the present invention is a novel platform for delivery of lipophilic drugs.

More specifically, the present inventors have developed a non-solvent-based lipophilic powder drug delivery system using the biodegradable microneedles which do not require a high-pressure injector and a special mucous membrane environment and serve as physical enhancers for the delivery of drugs through the skin and through which the powder-type lipophilic drug is administered through the layers of the skin. A particle size of the powder-type lipophilic drug is minimized using the smart polymer system composed of a polymer in which a colloidal structure is formed of a combination of hyaluronic acid and polyvinyl pyrrolidone at a ratio of 1:1. Such a colloidal structure is dispersed in the smart polymer system so that the colloidal structure is manufactured into biodegradable microneedles capable of overcoming the skin barrier and delivering the powder-type lipophilic drug. Such a smart polymer system (i) serves as the backbone of a biodegradable microneedle, and (ii) serves to minimize particles of the powder-type lipophilic drug, which is a target drug for transdermal administration, to uniformly load the powder-type lipophilic drug onto the biodegradable microneedles and enable the manufacture of the biodegradable microneedles, as shown in FIG. 1. The biodegradable microneedles to which the smart polymer system of the present invention is applied have improved drug delivery efficiency, compared to a solvent-dissolved lipophilic drug delivery system.

One of the best characteristics of the present invention is that the biodegradable microstructure of the present invention is a non-solvent drug delivery system which does not require a solvent used to dissolve the biodegradable microstructure. In the prior art, a composition constituting the microstructures should be melted or dissolved in a proper solvent to deliver a drug, but a solvent is not used for the microstructure of the present invention. That is, the smart polymer system (SPS) of the present invention may have the same effect as in the use of the solvent by enabling homogenization and nanoscaling of a powder-type drug using the smart polymer system (SPS) of the present invention.

Hereinafter, the viscous composition for transdermal drug delivery will be described in detail.

The viscous composition for transdermal drug delivery is characterized by including colloidal particles formed by a combination of a drug and a biodegradable polymer. Here, the biodegradable polymer includes a first amphiphilic polymer. In this case, the viscous composition for transdermal drug delivery is characterized by minimizing the use of a solvent. Preferably, the viscous composition may not include a separate solvent.

The drug may be a lipophilic drug or a water-soluble drug. In this case, the biodegradable polymer may be uniformly mixed and dispersed regardless of the water solubility/lipophilicity of the drug since the biodegradable polymer includes a first amphiphilic polymer having both hydrophilicity and hydrophobicity.

In the present invention, the term "lipophilic drug" is used as a meaning encompassing all of (i) a drug having an affinity to lipids, (ii) a drug having a stronger affinity to lipids or lipoids than water, (iii) a drug having an affinity to non-polar fluids, and (iv) a drug containing a functional group capable of being bound to lipids or lipoids.

Also, in the present invention, the term "water-soluble drug" is used as a meaning encompassing all of (i) a drug having an affinity to water, (ii) a drug having a stronger affinity to water than lipids or lipoids, (iii) a drug having an affinity to polar fluids, and (iv) a drug containing a functional group capable of being bound to water, contrary to the lipophilic drug.

The drug that may be used in the present invention is not particularly limited. For example, the drug includes a chemical, a pharmaceutical protein, a pharmaceutical peptide, nucleic acid molecules for gene therapy, nanoparticles, an active ingredient for functional cosmetics, and a cosmetic ingredient.

The drug that may be used in the present invention, for example, includes an anti-inflammatory agent, an analgesic agent, an antiarthritic agent, an antianxiety drug, an antidepressant, an antipsychotic drug, a tranquilizer, an antianxiety drug, a narcotic antagonist, an anti-Parkinson's disease drug, a cholinergic agonist, an anticancer drug, an anti-angiogenesis inhibitor, an immunosuppressant, an antiviral agent, an antibiotic, an appetite suppressant, an analgesic agent, an anticholinergic drug, an antihistaminic agent, an antimigraine agent, a pharmaceutical hormone, a coronary, cerebrovascular or peripheral vasodilator, a contraceptive pill, an antithrombotic drug, a diuretic drug, an antihypertensive drug, a cardioprotective agent, a cosmetic ingredient (for example, an anti-wrinkling agent, an anti-skin-aging agent, and a skin whitening agent), etc., but the present invention is not limited thereto.

A method of fabricating a microstructure according to one exemplary embodiment of the present invention is performed under non-heating treatment conditions, for example, performed at room temperature or a low temperature (for example, 5 to 20° C.) less than the room temperature. Therefore, although the drug used in the present invention is a drug vulnerable to heat, such as a pharmaceutical protein, a pharmaceutical peptide, nucleic acid molecules for gene therapy, etc., it is possible to fabricate the microstructure including the drug according to one exemplary embodiment of the present invention.

The drug includes drugs having a final powdery form includes, for example, a crystalline, semicrystalline or amorphous form. The smart polymer system (SPS) of the present invention may be applied to crystalline or semicrystalline drugs since the smart polymer system (SPS) causes the phase transition of the drug. However, the smart polymer system (SPS) of the present invention may also be applied to amorphous drugs since the smart polymer system (SPS) finally aims to (i) homogenize the drug and the biodegradable polymer and (ii) reduce the size of the colloidal particles formed of a combination of the drug and the biodegradable polymer.

Meanwhile, the crystalline or semicrystalline drug is phase-transitioned to an amorphous form due to a chemical bond or chemical interaction with the biodegradable polymer. The drug phase-transitioned to the amorphous form forms a colloidal structure with the biodegradable polymer.

That is, the colloidal particles may have a decreased colloidal particle size since the drug is phase-transitioned due to a chemical bond or chemical interaction between the drug and the biodegradable polymer.

According to one exemplary embodiment of the present invention, a hydroxyl group of capsaicin as the lipophilic drug and a carbonyl group in PVP as the biodegradable polymer form colloids via a chemical bond. Here, the chemical bond is a hydrogen bond.

In the present invention, the term, "biodegradable polymer" does not refer to a polymer that is directly or indirectly dissolved in a solvent or another material, but refers to a material that is used to improve the solubility of the drug, and thus is used to enhance the solubility of the drug by reducing a particle size of "colloidal particles" that are the finally formed structures of the drug and the biodegradable polymer. Meanwhile, the biodegradable polymer may be used in the same meaning as "dissolving polymer."

According to the present invention, the biodegradable polymer is characterized by including a first amphiphilic polymer, and may further include at least one polymer selected from the group consisting of a hydrophilic polymer, a hydrophobic polymer, and a second amphiphilic polymer in addition to the first amphiphilic polymer. According to one exemplary embodiment of the present invention, when the drug is a lipophilic drug, the biodegradable polymer may be formed of the first amphiphilic polymer and the hydrophilic polymer. On the other hand, when the drug is a water-soluble drug, the biodegradable polymer may be formed of a combination of the first amphiphilic polymer and the hydrophobic polymer.

According to a certain exemplary embodiment of the present invention, the biodegradable polymer may be formed of a combination of polyvinyl pyrrolidone and hyaluronic acid.

The first amphiphilic polymer and the second amphiphilic polymer that may be used in the present invention are distinguishable polymers, but may be the same as or different from each other. In this case, the first and second amphiphilic polymers may include at least one selected from the group consisting of various known amphiphilic polymers as polymers which are soluble in both polar and non-polar solvents such as, for example, polyvinyl alcohol (PVA), polyvinyl pyrrolidone (PVP), and chitosan.

The hydrophilic polymer that may be used in the present invention includes various known hydrophilic polymers as polymers that are soluble in a polar solvent. For example, the hydrophilic polymer includes at least one monomer selected from the group consisting of hyaluronic acid (HA), carboxymethyl cellulose (CMC), methacrylic acid (MA), 2-hydroxyethyl methacrylate (HEMA), ethyl acrylate (EA), 1-vinyl-2-pyrrolidinone (VP), propenoic acid 2-methyl ester (PAM), monomethacryloyloxyethyl phthalate (EMP), and ammonium sulphatoethyl methacrylate (SEM).

The hydrophobic polymer that may be used in the present invention includes various known hydrophobic polymers as polymers that are soluble in a non-polar solvent. For example, the hydrophobic polymer includes at least one monomer selected from the group consisting of methyl methacrylate (MMA), acrylonitrile (AN), methacryloxypropyltris(trimethylsiloxy)silane (TRIS), and 2,2,2-trifluoroethylmethacrylate (TRIF).

In the present invention, a biodegradable polymer system is used for transdermal drug delivery. Here, a proper combination of polymers is required so that the biodegradable polymer including the first amphiphilic polymer surrounds the lipophilic drug to form colloidal particles. In the present invention, a combination of polymers used to from the colloidal particles includes (i) the first amphiphilic polymer and the hydrophilic polymer, (ii) the first amphiphilic polymer and the hydrophobic polymer, or (iii) the first amphiphilic polymer and the second amphiphilic polymer at a weight ratio of 20:1 to 1:20. According to the present invention, the weight ratio may be in a range of 15:1 to 1:15 or 10:1 to 1:10. According to one exemplary embodiment of the present invention, the weight ratio is in a range of 5:1 to 1:5.

According to another exemplary embodiment of the present invention, the biodegradable polymer may be formed of a combination of the first amphiphilic polymer and the hydrophilic polymer at a weight ratio of 2:1 to 1:2. According to a certain exemplary embodiment of the present invention, the biodegradable polymer may be formed of a combination of the first amphiphilic polymer and the hydrophilic polymer at a weight ratio of 1:1.

The viscous composition for transdermal drug delivery refers to a composition having an ability to be transformed to form microstructures, and shows viscosity. The viscosity of the viscous composition for transdermal drug delivery may be widely varied according to the type, concentration or temperature of the drug and the biodegradable polymer included in the composition, or the addition of a viscosity modifying agent, and may be properly adjusted according to a purpose of the present invention. The viscosity of the viscous composition for transdermal drug delivery may be adjusted by an innate viscosity of a viscous material, may also be adjusted using an additional viscosity modifying agent in the viscous composition for transdermal drug delivery.

For example, a viscosity modifying agent typically used in the related art such as, for example, a viscosity modifying agent such as hyaluronic acid and salts thereof, polyvinyl pyrrolidone, a cellulose polymer, dextran, gelatine, glycerine, polyethylene glycol, polysorbate, propylene glycol, povidone, carbomer, gum ghatti, guar gum, glucomannan, glucosamine, a dammar resin, rennet casein, locust bean gum, microfibrillated cellulose, psyllium seed gum, xanthan gum, arabinogalactan, Arabia gum, alginic acid, gelatine, gellan gum, carrageenan, karaya gum, curdlan, chitosan, chitin, tara gum, tamarind gum, tragacanth gum, furcelleran, pectin, or pullulan, may be added to a composition including a main component of the microstructure, for example, a biocompatible material to properly adjust the viscosity of the viscous composition according to the present invention. Preferably, a composition of colloidal particles used in the present invention has a viscosity of 200,000 cSt or less.

Meanwhile, the colloidal particles formed of a combination of the drug and the biodegradable polymer according to the present invention may be amorphized by a chemical bond or chemical interaction between the lipophilic drug and the biodegradable polymer, or may have a decreased particle size. In this case, the colloidal particles are in a final amorphous or non-crystalline form.

In the polymer system according to the present invention, the most important factor affecting the crystallization of the drug is the interaction between the drug and an additive (i.e., a biodegradable polymer). The biodegradable polymer may provide a binding site for the drug for being stabilized in an amorphous form to hinder the crystallization.

All types of characteristics required to load a powder-type drug onto the microneedles, such as amorphization, uniformity and a decrease in size of the powder-type drug, and a sufficient strength to manufacture the microstructures, cannot be easily realized for homopolymers. On the other hand, a combination of two or more biodegradable polymers may provide a hydrogen bond for amorphization which contributes to reducing a particle size as well as a mechanical strength to the microstructures. Therefore, the present inventors have developed a smart polymer system by combining polymers having different characteristics, and found that the development of such a system leads to amorphization and a decrease in the particle size of particles of the drug In the present invention, the term "colloidal particle" refers to a particle which includes a drug at a core thereof, and a biodegradable polymer including a first amphiphilic polymer surrounding the drug. That is, the colloidal particle may have a core-shell structure in which the biodegradable polymer surrounds the drug. For example, when the drug is a lipophilic drug and the biodegradable polymer is a combination of the first amphiphilic polymer and a hydrophilic polymer, a hydrophobic moiety of the first amphiphilic polymer is bound to the lipophilic drug, and a hydrophilic moiety of the first amphiphilic polymer is bound to the hydrophilic polymer present outside the particles to finally form the colloidal particles in which a layer of 'the lipophilic drug, the first amphiphilic polymer and the hydrophilic polymer' is formed outwardly from the center. On the other hand, when the drug is a water-soluble drug and the biodegradable polymer is a combination of the first amphiphilic polymer and a hydrophobic polymer, a hydrophilic moiety of the first amphiphilic polymer is bound to the water-soluble drug, and a hydrophobic moiety of the first amphiphilic polymer is bound to the hydrophobic polymer present outside the particles to finally form the colloidal particles in which a layer of 'the water-soluble drug, the first amphiphilic polymer and the hydrophobic polymer' is formed outwardly from the center.

The chemical bond or chemical interaction between the drug and the biodegradable polymer means that a functional group of the drug and a functional group of the biodegradable polymer are bound to each other via a chemical bond. For example, a hydrogen bond between an amide carbonyl group of the polymer and a hydrogen donor moiety of the drug serves to hinder the crystallization of the drug and maintain an amorphous state (27).

According to the present invention, a carbonyl group of PVP that is an amphiphilic polymer, and a hydroxyl group of the lipophilic drug form a hydrogen bond to contribute to the amorphization of the crystalline lipophilic drug.

The size of the colloidal particles is not particularly limited, but may be in a range of 50 nm to 1,000 μm according to the types of the drug and the biodegradable polymer. According to one exemplary embodiment of the present invention, the colloidal particles may have a size of 50 nm to 300 nm, and, according to a certain exemplary embodiment of the present invention, the nano-sized colloidal particles may have a size of 100 nm to 200 nm (see FIGS. 2C to 2H).

Specifically, the present inventors have conducted research on an amorphization mechanism of the above-described lipophilic drug, and found that the crystalline drug is changed into an amorphous form when the drug interacts with the amphiphilic polymer (for example, PVP), which contributes to the improvement in solubility of the drug. That is, a decrease in a degree of crystallinity of the drug indicates an increase in the solubility of the powder-type drug.

Method of Preparing a Viscous Composition for Transdermal Drug Delivery

The present invention provides a method of preparing a viscous composition for transdermal drug delivery, which includes homogenizing a drug in a biodegradable polymer including a first amphiphilic polymer to form colloidal particles.

First of all, the drug, the biodegradable polymer including the first amphiphilic polymer, and the colloidal particles are as described in detail.

The method of preparing a viscous composition for transdermal drug delivery may include homogenizing the drug in the biodegradable polymer including the first amphiphilic polymer to form the colloidal particles. In this case, the amphiphilic polymer is characterized by having both hydrophilicity and lipophilicity. Therefore, the biodegradable polymer may be uniformly mixed and dispersed regardless of the water solubility/lipophilicity of the drug.

The method of preparing a viscous composition for transdermal drug delivery has effects of (i) easily homogenizing the drug in the biodegradable polymer including the first amphiphilic polymer, and thus (ii) reducing a size of the colloidal particles (nanoscaling) since the smart polymer system (SPS) of the present invention itself is applied to the method.

The homogenization is a process of uniformly mixing and dispersing the drug and the biodegradable polymer, a goal of which is to finally homogenize the drug and reduce a size of the colloidal particles. The homogenization may be performed using a method such as simple dispersion, mechanical dispersion, ultrasonic dispersion, or a combination thereof. Meanwhile, a proper emulsifying agent may also be added to perform the homogenization on the condition that the emulsifying agent has no influence on formation of the drug, the biodegradable polymer including the first amphiphilic polymer, and the colloidal particles.

Microstructure Device

The present invention provides a microstructure device for processing a viscous composition for transdermal drug delivery. Here, the microstructure device includes a substrate, and microstructures formed on the substrate, and each of the microstructures includes colloidal particles formed of a combination of a drug and a biodegradable polymer including a first amphiphilic polymer.

First of all, specific contents of the viscous composition for transdermal drug delivery are as described above.

The microstructures may be in various forms, and may be microneedles, microblades, microknives, microfibers, microspikes, microprobes, microbarbs, microarrays, or microelectrodes, and preferably microneedles, but the present invention is not limited thereto.

The microstructures may have various dimensions. For example, the microstructures according to the present invention have a tip diameter of 1 to 500 μm, 2 to 300 μm, or 5 to 100 μm, and an effective length of 100 to 10,000 μm, 200 to 10,000 μm, 300 to 8,000 μm, or 500 to 2,000 μm. The term "tip" of the microstructure used in this specification refers to one end portion of the microstructure having the minimum diameter. The term "effective length" used in this specification refers to a vertical length from a tip of the microstructure to a surface of a support. The term "bottom part" used in this specification refers to one end portion of the microstructure having the maximum diameter. For example, the microstructures according to the present invention have a bottom diameter 50 to 1,000 μm and an effective length of 100 to 10,000 μm.

The microstructure device is a device which is separable from a substrate configured to support the microstructures so that only the microstructures are easily injected into the skin. For example, when a force is applied to the substrate on which the microstructures are formed, the force serves to separate the microstructures from the substrate and also serves to allow the separated microstructures to have kinetic energy so that the separated microstructures can be injected into the skin. Based on this principle, the microstructures according to the present invention pass through the transdermal layer.

Holes may be formed in the substrate on which the microstructures are fabricated, and the microstructures are fabricated on the substrate to be supported by immediately adjacent planes of the holes of the substrate. The substrate serving as a support layer provides a support plane on which the microstructures may be fabricated. After the microstructures are injected into the skin, the holes of the substrate serve to easily separate the microstructures from the substrate.

When the viscous composition for transdermal drug delivery is spotted on the holes of the substrate, most spots have a lager diameter than the holes. Since the spots are viscous due to the viscosity of the drug and polymer themselves even when the spots have a smaller diameter than the holes, the spots may be attached to immediately adjacent inner planes (inner lateral planes) of the holes. When the spots are extended, the microstructures may be fabricated on the substrate to be supported by immediately adjacent planes (including both immediately adjacent outer planes of the holes and inner lateral planes of the holes) of the holes of the substrate.

The extension of the spots may be performed using various methods. For example, the microstructures may be fabricated by bringing a frame having protrusions into contact with spots and then drawing the spots upwards using a method as disclosed in Korean Patent No. 0793615 previously filed by the present inventors. Also, the microstructures may be fabricated by applying a negative pressure to the spots as disclosed in Korean Unexamined Patent Application Publication No. 2013-0019247 previously filed by the present inventors. In addition, the microstructures may be fabricated by applying a centrifugal force to the spots as disclosed in Korean Patent No. 1590172 previously filed by the present inventors.

The microstructure device may be mainly manufactured by two methods:

In the first method, when the substrate has no holes, the viscous composition for transdermal drug delivery is coated or spotted on a surface of the substrate. Thereafter, the composition is extended to fabricate the microstructures using the method disclosed in Korean Patent Nos. 0793615 and 1590172 previously filed by the present inventors and the method disclosed in Korean Unexamined Patent Application Publication No. 2013-0019247.

In the second method, when the substrate has the holes, the microstructures are fabricated on a surface of the substrate to be supported by immediately adjacent planes of the holes of the substrate serving as a support layer. For example, when the viscous composition for transdermal drug delivery is spotted on the holes of the substrate, most of the spots have a larger diameter than the holes. Since the spots have a predetermined viscosity even when the spots have a smaller diameter than the holes, the spots may be attached to immediately adjacent inner planes of the holes. When the spots are extended, the microstructures may be fabricated on the substrate to be supported by immediately adjacent planes of the holes of the substrate. The extension of the spots may be performed by various methods, for example, performed by the method disclosed in Korean Patent Nos. 0793615 and 1590172 previously filed by the present inventors, and the method disclosed in Korean Unexamined Patent Application Publication No. 2013-0019247.

According to one exemplary embodiment of the present invention, the microstructures are separated from the substrate to be shot due to a pushing pressure transmitted to the bottom parts of the microstructures through the substrate (for example, the holes of the substrate).

In this specification, the term "shooting" used with reference to the microstructures means that the microstructures are separated from the substrate to move forward.

When the pushing pressure is applied to the bottom parts of the microstructures, the microstructures have a weaker coupling strength than the microstructures coupled to a typical substrate. As a result, the microstructures are relatively easily separated from the substrate to be shot. The pushing pressure may include any type of pushing pressure as long as it acts to separate the microstructures from the substrate to move forward. The pushing pressure may be generated and applied by various methods. For example, a pushing pressure may be generated and applied using the air or an article (for example, a bar). The pushing pressure used in the present invention includes a pressure caused by various types of force, for example, a physical pressure or a chemical pressure. For example, the physical pressure includes a pressure caused by the air, a pressure caused by a mechanical force, a pressure caused by elasticity, and a physical force (i.e., a finger force) by human beings, but the present invention is not limited thereto. The chemical pressure includes a pressure caused by changes in temperature, volume, viscosity, surface tension, concentration or chemical structure by a chemical reaction and the addition of a compound, but the present invention is not limited thereto.

According to one exemplary embodiment of the present invention, the microstructure device may further include a pushing pressure generation unit configured to transmit a pushing pressure to the holes.

In the microstructure device, the substrate may be manufactured using various materials. For example, the substrate may be manufactured using a material such as a polymer, an organic chemical material, a metal, a ceramic, a semiconductor material, etc. The material that may be used in the substrate will be described with reference to the polymer and the biocompatible material used to fabricate the microstructures.

The substrate may be manufactured using a material which is the same as or different from that of the microstructures. The thickness of the substrate is not particularly limited, and is, for example, in a range of 0.1 to 1,000 µm, 1 to 100 µm, 1 to 50 µm, or 1 to 10 µm. According to one exemplary embodiment of the present invention, the substrate may be manufactured using a metal or an organic chemical material.

In the microstructure device, the size of holes formed in the substrate is not particularly limited. For example, the diameter of the holes is in a range of 10 to 5,000 µm, 100 to 4,000 µm, 500 to 4,000 µm, 800 to 4,000 µm, 800 to 3,000 µm, 900 to 2,000 µm, or 900 to 1,500 µm. The holes may be introduced by various methods. For example, the holes may be introduced using a laser cutting device.

In the microstructure device, the substrate on which the viscous composition for transdermal drug delivery is spotted has a plurality of holes. The plurality of holes may have a diameter smaller or larger than the bottom parts of the microstructures. When the plurality of holes have a smaller diameter than the bottom parts of the microstructures, the microstructure device is favorable for directly fabricating the microstructures on a main layer. On the other hand, when the plurality of holes have a larger diameter than the bottom parts of the microstructures, it is desirable to fill the holes of the substrate, fabricate the microstructures and then remove the filling so as to fabricate the microstructures.

According to one exemplary embodiment of the present invention, regions of the substrate on which the microstructures are fabricated have a weaker strength than the other regions of the substrate. The microstructures may be more effectively shot due to such weak and strong pattern coating.

The microstructure device may be manufactured with a certain alignment array (see FIG. 4).

The microstructure device may be manufactured for a single use. When the microstructure device is manufactured for a single use, the microstructure device further includes a sealing film (i.e., a sealer) detachable from the device and configured to protect the microstructures from external environments. The corresponding device has to be discharged after use since the device is a dispensable system.

Advantageous Effects

The characteristics and advantages of the present invention are summarized as follows:

(a) The present invention relates to a viscous composition for transdermal drug delivery which includes colloidal particles formed of a combination of a drug and a biodegradable polymer, wherein the biodegradable polymer includes a first amphiphilic polymer, a method of preparing the same, and a microstructure device using the same.

(b) According to the present invention, the use of a solvent is minimized to homogenize the drug in the biodegradable polymer including the first amphiphilic polymer, thereby forming colloidal particles.

(c) According to the present invention, since a separate solvent cannot be used, the microstructure device should be a transdermal drug delivery system which is safe, efficient or useful for drugs which do not include a proper solvent, show poor bioavailability or have a high molecular weight.

DESCRIPTION OF DRAWINGS

The above and other objects, features and advantages of the present invention will become more apparent to those of ordinary skill in the art by describing in detail exemplary embodiments thereof with reference to the accompanying drawings, in which:

FIG. 1B is a schematic view more specifically showing a smart polymer system (SPS) for powder-type lipophilic drug delivery through biodegradable microneedles according to one exemplary embodiment of the present invention. In a combination of smart polymer molecules, that is, hyaluronic acid (HA) and polyvinyl pyrrolidone (PVP), both of which are used to form a colloidal structure, a microsized crystalline drug is transformed into a nanosized amorphous form. SPS increases the formation of the colloidal structure through the interaction of a hydrophobic PVP chain and a hydrophilic HA chain via a hydrogen bond. When the smart polymer designed for biodegradable microneedles is inserted into the skin, the smart polymer may be dissolved, and a lipophilic drug-based powder may then be dispersed.

FIG. 1C is a diagram showing a smart polymer system (SPS)-based biodegradable microneedle for transdermal lipophilic drug delivery. The left panel shows a SPS-based microneedle using a powdery model drug, and the right panel shows the dispersion of the powder into skin layers through the SPS-based biodegradable microneedle.

FIG. 2 shows characteristics of a smart polymer system designed for the biodegradable microneedles according to one exemplary embodiment of the present invention, and a colloidal structure. FIG. 2I shows the results of the Fourier transform infrared spectroscopy (FTIR) analysis of NR and CAP, and other different polymers. A blue block represents a C=O bond, and a pink block represents an O—H bond.

FIG. 4 shows in vitro analysis results using Franz cell analyses of microneedles to which the SPS of the present invention is applied, and NR and CAP microneedles designed through the SPS. The microneedles are fabricated using a drawing lithography method. FIG. 4A (i) is a scanning electron microscope (SEM) image showing a form and tip portions of NR. FIG. 4A (ii) is a bright field image of a microneedle array. FIG. 4A (iii) is an image observed from a top view of pig skin after the NR microneedles are inserted into the pig skin. Red circles represent insertion portions. FIG. 4A (iv) shows a vertical section after a NR microneedle is inserted into the skin. Pink spots indicate that NR is dispersed into the skin.

FIG. 5 shows analysis results of an in vivo effect of the CAP Mn. A decrease in the severity of arthritis in CIA mice is observed when CAP Mn is applied once a week after 21 days of immunization. In FIG. 5A (ii), red regions represent regions in which a bone volume (BV) is measured.

FIGS. 6A and 6B are scanning electron microscope (SEM) images when the SPSs of NR and CAP are not used, respectively. The crystalline material has a decreased particle size, and is transformed into an amorphous form due to combinating with a biodegradable polymer. Scale bar: 1 μm.

FIG. 7A (i) shows an scanning electron microscope (SEM) image on which irregular NR microneedle structures are able to be observed. Here, a relatively wide tip portion of the NR microneedle is formed due to limitations on NR crystals having a larger size. Scale bar: 10 μm. FIG. 7A (ii) shows an SEM image on which a crystalline drug (white arrows) is embedded when the SPS of the present invention is not used. A crystal structure of NR is kept intact, which serves as a main cause of the irregular structure when the microneedles are fabricated. Scale bar: 1 μm. FIG. 7B shows results obtained by testing the permeation of the crystalline NR microneedle structure into the skin. FIG. 7B (i) shows that irregular structures are observed on the skin when a microcrystalline drug is inserted into the skin. It can be seen that the drug still remains on a surface of the skin. FIG. 7B (ii) is a vertical cross-sectional view showing that the irregular microneedles are delivered into the skin. It can be seen that the NR crystals remain on the surface of the skin. Scale bar: 500 μm.

MODES OF THE INVENTION

Figure 1A:
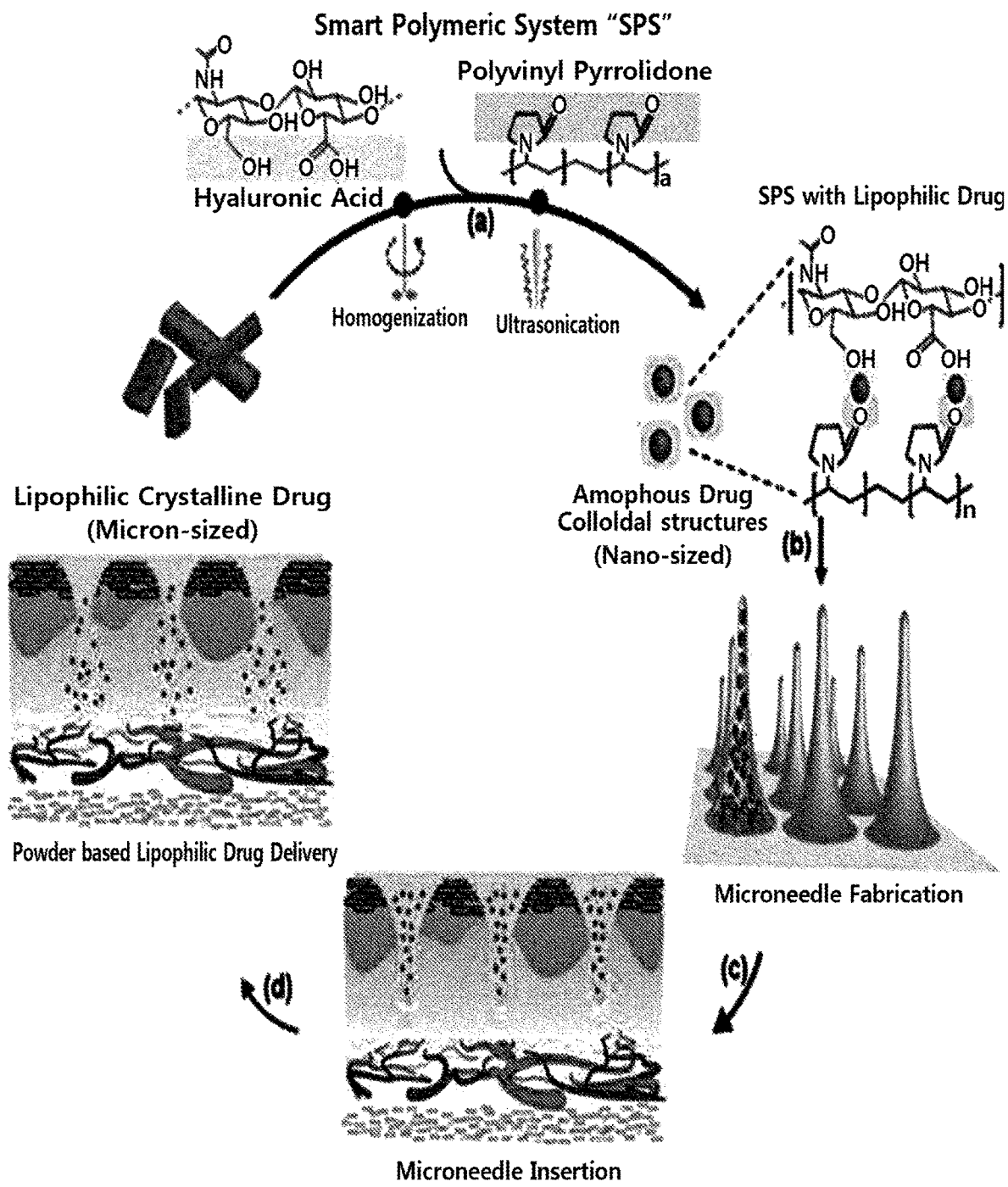
FIG. 1A is a schematic view of a 'smart polymer system' designed for biodegradable microneedles for transdermal delivery of a powder-based lipophilic drug. (a) In a smart polymer system having a combination of smart polymers according to one exemplary embodiment of the present invention, particularly, a combination of hyaluronic acid (HA) and polyvinyl pyrrolidone (PVP) at a ratio of 1:1, a microsized crystalline drug is transformed into a nanosized amorphous form. (b) Smart polymer particles (droplets) including an amorphous lipophilic drug are formed on a base substrate. (c) Biodegradable microneedles are fabricated. (d) A smart polymer designed for biodegradable microneedles is inserted into the skin. (e) The smart polymer is dissolved, and the powder-based lipophilic drug is then dispersed into the skin.

Exemplary embodiments of the present invention will be described in detail below with reference to the accompanying drawings. While the present invention is shown and described in connection with exemplary embodiments thereof, it will be apparent to those skilled in the art that various modifications can be made without departing from the scope of the invention.

Unless specifically stated otherwise, all the technical and scientific terms used in this specification have the same meanings as what are generally understood by a person skilled in the related art to which the present invention belongs. In general, the nomenclatures used in this specification and the experimental methods described below are widely known and generally used in the related art.

EXAMPLES

Experimental Materials

Carboxymethyl cellulose (CMC having a molecular weight of 90 kDa), polyvinyl alcohol (PVA having a molecular weight of 1,300 kDa), polyvinyl pyrrolidone (PVP having a molecular weight of 30 to 60 kDa), 3-(4,5-dimethylthiazol-2-yl)-2,5-diphenyltetrazolium bromide (MTT), and reagents Nile Red (318.369 g/mol) and capsaicin (305.41 g/mol) were purchased from Sigma Aldrich (USA). Sodium hyaluronate (HA having a molecular weight of 29 kDa) was purchased from Soliance (France). Bovine type II collagen was purchased from Chondrex (USA). A complete Freund's adjuvant (CFA) and an incomplete Freund's adjuvant (IFA) were purchased from Sigma Chemicals (USA). A Westergren pipette was purchased from Fisherbrand (USA). Mouse TNF-α, IL-1β, and IL-6 ELISA kits were purchased from Invitrogen (USA). A GM-CSF ELISA kit was purchased from Affymatrix (USA).

Experimental Methods

1. Particle Size Analysis

Particle size analysis was performed using a particle size analyzer (Schimdzu, Japan). Polymer combinations of CMC and PVA, CMC and PVP, CMC and HA, PVA and PVP, PVA and HA, and PVP and HA were prepared together with 0.1%

Nile Red (NR) and 0.75% capsaicin (CAP) at ratios of 1:1, 1:2, 2:1, 1:3, 3:1, 1:4, 4:1, 1:5, and 5:1, respectively, to screen the polymers. To uniformly mix drugs having a polymer combination and a colloid formulation, the drugs were homogenized at an optimum rotary speed of 21,000 rpm for 5 minutes using a rotor homogenizer (Homogenizer Power Gen 500, Fisher Scientific, USA). Ultrasonication was performed at 20 KHz±50 KHz using an ultrasonicator (Sonic vibra cell, USA). In the size analysis, distilled water was used as a solvent, and an average of values obtained reading each of samples three times was calculated. The particle size reading was performed at an interval of 30 minutes due to the tendency of the drug to be crystallized when the drug is exposed to distilled water for a long period of time.

2. Characterization of Morphology of Powdery Drug in Colloidal Structure of Polymer The morphology of a colloidal structure of a polymer was analyzed using a scanning electron microscope (SEM; equipped with Type JEOL (JSM-7001F) energy-dispersive X-ray (EDX) Oxford ISIS 300 micro-analysis system). For this experiment, platinum coating was performed at 10 mA to protect colloids from high-energy beams. Also, a decrease in the size of the colloids was confirmed using a transmission electron microscope (TEM), and this confirmation was performed on a very thin sample formed on a copper grid as an upper cover provided in the grid. A TEM micrograph was obtained at 120 kV using a JEM 2010 (HC) (JEOL Ltd, USA) microscope. The amorphous form of the drug in the colloidal structure was confirmed using a random XRD analysis on the sample, and continuously scanned at intervals of 3-80° 2θ using an Ultima IV diffractometer (Rigaku Corporation, Japan) with Bragg-Brentano geometry (2θ/θ) having 40 kV/30 mA X-ray and K-beta filter radiations.

3. Study on Drug-Polymer Interaction

Interactions between a drug and various polymer combinations were analyzed using a Vertex 70 (Burker, USA) FT-IR spectrometer. In the combination of the drug and each of the polymers, the infrared spectra were obtained in a range of 4000-400 $cm^{-1}$. A KBr beam splitter was used, and a degree of resolution higher than 0.4 $cm^{-1}$ was obtained using a wavenumber accuracy of 0.1% T or more. 10% by weight of all the polymers were analyzed in a non-organic solvent (distilled water).

4. Fabrication of Microneedles by Drawing Lithography

The present inventors have fabricated biodegradable microneedles in a 5×5 array.

That is, a basic plate was coated with CMC. A dispenser was used to drop droplets on the CMC-coated plate. The droplets form smart polymer systems, for example, lipophilic drugs (0.1% NR and 0.75% CAP), each of which was composed of HA and PVP at a ratio of 1:1. An array of the droplets was formed approximately every 6 seconds at a speed of 60 mm/s, and dried for 8 minutes. Therefore, cylindrical structures having a height of 600 μm and a slope formed at a central region thereof are fabricated. Here, a tip portion of the structure had a diameter of 35 μm. A sloped tip was separated by drawing the structure at a speed of 75 mm/s or more. It was possible to form a microneedle array on the basic plate on which images were able to be formed using a CCD camera (Samwon, South Korea).

5. In Vitro Analysis

In vitro analysis was performed using Franz cell diffusion. Microneedles containing 0.1% NR and 0.75% CAP were applied onto the skin of a dead pig, and put on donor moieties of Franz cells. A receptor moiety was composed of PBS including 20% ethanol. A sample was analyzed at intervals of 0, 0.5, 1, 2, 3, 4, 5, 6, 12, and 24 hours. The quantification of NR and CAP was performed at 559 nm and 280 nm using UV-Vis spectroscopy (Jasco, V650) and Ultra Performance Liquid Chromatography (UPLC) (Acquity UPLC, Waters), respectively. The amounts of NR and CAP in a microneedle patch were determined by dissolving the patch in PBS including 10% ethyl acetate and 20% ethanol, respectively. Thereafter, solid-phase extraction was performed using ethyl acetate as an eluent. A microneedle patch having no drug was used as the control. 0.1% NR dissolved in 20% ethyl acetate and CAP dissolved in 40% ethanol were used in a topical formulation model. This model was most widely used for a formulation of a lipophilic compound in which an organic solvent was used to dissolve the lipophilic drug. 1 mL of such a topical formulation was dropped on the skin of a pig until the topical formulation was diffused to an area of approximately 2 $cm^2$.

6. In Vivo Analysis

All animals were treated according to the 'guidelines and regulations for the use and care of animals' by Yonsei University (Seoul, Korea). The onset of arthritis was induced in six-week-old female DBA/1 mice (Taconic, Korea), and the DBA/1 mice were then adapted to circumstances for a week. The mice were fed with standard feed and water, divided into 4 groups (n=8), and bred in a cage lined with sawdust. Bovine type II collagen was dissolved in 0.05 M acetic acid, and mixed overnight at 4° C. The resulting solution was mixed with a complete Freund's adjuvant (CFA) at a ratio of 1:1 in the presence of 1 mg/ml of M. tuberculosis to form an emulsion. Primary immunization was performed by subcutaneously injecting 100 microliters (μL) of the emulsion into a lower part of a mouse's tail. After 21 days, an equivalent amount of the emulsion including bovine type II collagen and an incomplete Freund's adjuvant (IFA) was administered to promote an immune response.

After the promotion of the immune response, 0.75% CAP microneedle and topical CAP treatments were performed in the $4^{th}$ week, and this experiment was then continued for 6 weeks. CAP microneedles were administered into the hind legs of the CIA mice suffering from arthritis three times a week. The same amount of the topical CAP was administered to the hind legs three times a week, and the topical CAP administration was performed using an adhesive. PBS was intraperitoneally injected three times into the control mouse group.

To measure an erythrocyte sedimentation rate (ESR), a modified Westergren method was used. Four equivalents of an anti-blood coagulation factor EDTA was diluted with an equivalent of saline, and mixed. The resulting solution was transferred using a Westergren pipette, and kept in a vertical posture for an hour. The number of erythrocytes per milliliter was reduced within this time to present the ESR.

All the 20 mice were divided into 4 groups, and then subjected to a micro-CT imaging experiment. A leg of a laboratory mouse was scanned to reconstruct a three-dimensional (3D) structure using micro-CT (Bruker Skyscan, USA). Arthritis induction, treatment schedule and animal sacrifice were carried out according to the same method as described above. Concentrations of tumor necrosis factor-α (TNF-α), interleukin 1β (IL-1β, interleukin 6 (IL-6) sera were measured using solid-phase sandwich ELISA (Invitrogen, MD, USA).

7. Statistical Analysis

Statistical comparison was performed on three or more groups using a one-way analysis of variance (ANOVA) (P≤0.05).

Experimental Results

1. Design of Smart Polymer System (SPS)

To design a smart polymer system (SPS), a decrease in the size of a powder-type lipophilic drug, and the phase transition were examined. Thereafter, the SPS was collected to be mounted in a microneedle for transdermal delivery, as shown in FIGS. 1B and 1C. In an experiment for proving the lipophilic powder drug delivery using the SPS, the present inventors have selected Nile Red (NR) having a log P of 5(8), that is, high lipophilicity as a lipophilic dye, and lipophilic drug capsaicin (CAP) having a log P of 4.0(9) as a potential candidate drug for inflammation-related pathological conditions of arthritis.

The sizes of commercially available crystalline NR and CAP were 6.723±5 μm and 4.845±3 μm, respectively. However, after the size of NR was homogenized, the size of NR decreased to 1.797±7 μm and the size of CAP decreased to 0.986±6 μm. The present inventors have assumed that the decrease in particle size was able to be achieved through the SPS based on size-dependent screening of an ideal combination of polymers. To achieve the above objectives, the present inventors have developed an SPS capable of making use of various chemical availabilities of a hydrophilic, lipophilic and amphiphilic biodegradable polymer. The biodegradable polymer system is used to enhance the solubility of a drug which is poorly soluble in water (11). Also, such a system has been widely used as a microneedle backbone (12). Based on these facts, four biodegradable polymers were selected, and used as microneedle matrixes. Hyaluronic acid (HA) and carboxymethyl cellulose (CMC) were selected as three hydrophilic polymers, and polyvinyl alcohol (PVA) and polyvinyl pyrrolidone (PVP) were selected as amphiphilic polymers. Among these, polyvinyl pyrrolidone (PVP) was used as a template of the SPS. Hyaluronic acid was selected due to its nature to be used as an electrolyte due to acid hydrolyzability, CMC was selected due to high hydrophilicity which aids in the formulation of the microneedle matrix, and PVA was a well-known surfactant which enhanced the solubility of the lipophilic drug. PVP was selected due to amphiphilicity, thereby providing a property as a hydrophilic polymer as well as a hydrophobic polymer and also providing a crystal positioning effect of PVP to inhibit the recrystallization of the lipophilic drug.

10% by weight of HA, CMC, PVA and PVP were homogenized, and ultrasonicated with 0.1% NR and 0.75% CAP to form a uniformly dispersed solution.

The hydrodynamic diameters of NR and CAP homogenize with HA, CMC, PVA and PVP were listed in Table 1. It was apparent that the particle sizes of NR and CAP homogenized with the hydrophilic polymers such as HA and CMC increased because the drug aggregated under the hydrophilic environments of HA and CMC. Also, PVA had an effect of reducing a decrease in size of NR and CAP, compared to PVP. This is assumed to be due to the biodegradability of PVP by an amphiphilic side chain which did not exist in the PVA. Although the particle sizes of PVA and PVP were observed to be small, the particle sizes of PVA and PVP did not reach a nanometer size range, indicating that the size of the powder-type lipophilic drug was not sufficiently reduced only by each of the polymer systems. However, the smart polymer system (SPS) of the present invention having both chemical characteristics of lipophilic and hydrophilic polymers was able to be used to solve the above problems (see the following Examples).

TABLE 1

Effects of biodegradable polymer on particle sizes of NR and CAP

| Polymer compositions | NR particle size (μm) | CAP particle size (μm) |
|---|---|---|
| None | 1.797 ± 7 | 0.986 ± 6 |
| HA | 11.083 ± 4 | 9.736 ± 2 |
| CMC | 67.733 ± 8 | 43.856 ± 3 |
| PVA | 4.243 ± 8 | 2.676 ± 7 |
| PVP | 1.564 ± 3 | 1.432 ± 3 |

2. Analysis of Smart Polymer System and Colloidal Structure Designed for Microneedles To check a combination for SPS capable of adjusting the particle size of the lipophilic drug.

Figure 2A:
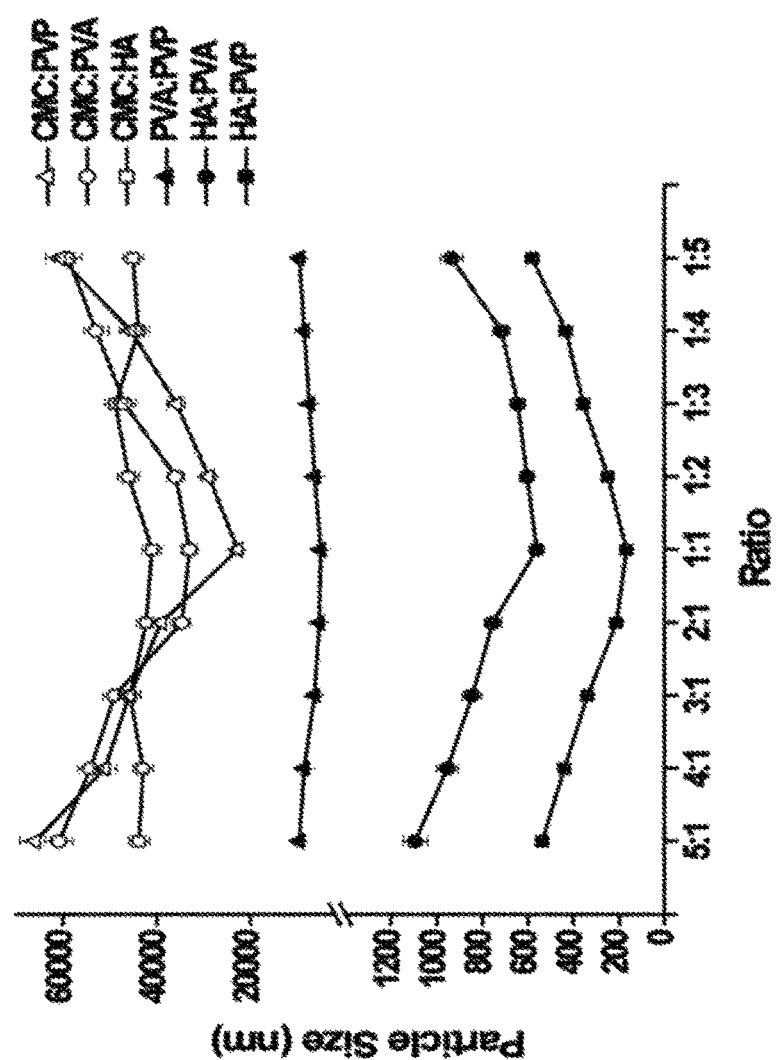
FIGS. 2A and 2B show suitable combinations of CMC, HA, PVA and PVP to minimize a particle size of each of Nile Red (NR) and capsaicin (CAP), and particle size distributions thereof.
Figure 2B:
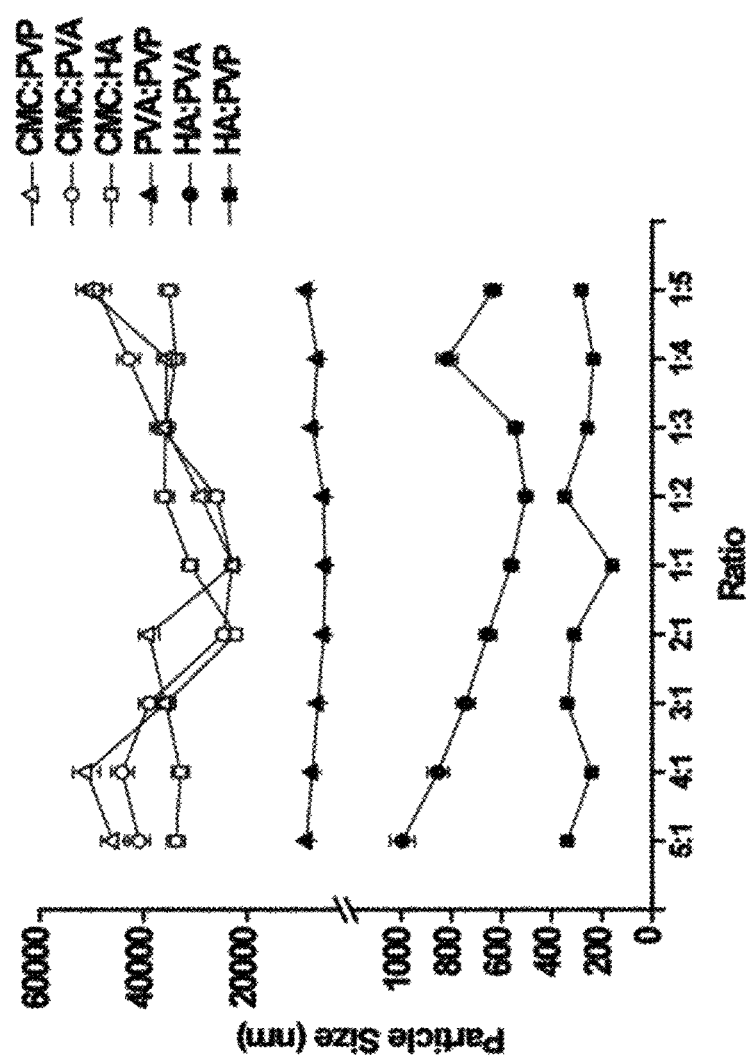

For the combinations of CMC and PVP, HA and PVP, CMC and PVA, HA and PVA, PVP and PVA, and CMC and HA which were present at each of weight ratios of 5:1, 4:1, 3:1, 2:1, 1:1, 1:2, 1:3, 1:4, and 1:5, the particle sizes of NR and CAP were analyzed (FIGS. 2A and 2B). Importantly, the smallest particle size was observed in the combination of HA and PVP which were present at a weight ratio of 1:1 among all the polymer systems.

However, it was revealed that the particle sizes of the combinations including CMC were higher at all the weight ratios due to high viscosity and a water retention property acting on the aggregation of the lipophilic drug, compared to the combinations including no CMC. The previous studies showed that the surface activity of PVA plays an important role in the dissolution of the lipophilic drug (13). Surprisingly, the particle size of PVA in most of the combinations of CMC and HA was in a micrometer range, indicating that the solubility was hindered in the presence of the hydrophilic polymer. Also, it was revealed that the particle size in most of the combinations including the hydrophilic polymer increased, as in such a hydrophilic polymer forming a hydrophilic environment around the lipophilic drug which tended to aggregate to minimize an area on which an inner core of the lipophilic drug was formed and which comes in contact with an outer surface of the lipophilic drug. On the other hand, HA and PVP (1:1) had the smallest particle sizes of 157.4±6 nm in the case of NR and 167.4±4 nm in the case of CAP because of the hydrophobicity of PVP which increments an interaction with the lipophilic drug via a chemical functional group, as described above. Therefore, the decrease in particle size as the first criterion for designing of the SPS was satisfied due to the optimal ratio (1:1) of the polymer compositions (HA and PVP).

Figure 2D:
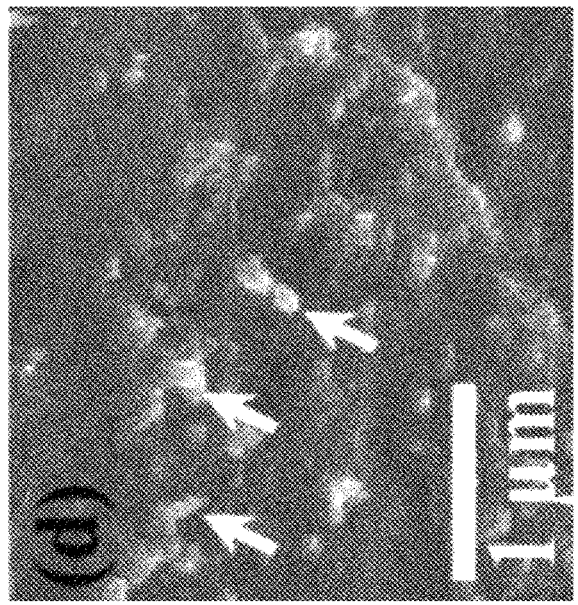
FIGS. 2C to 2E show morphological characteristics of (c) colloids formed of HA and PVP at a ratio of 1:1 without NR and CAP, and colloids formed together with (d) NR or (e) CAP. The embedded colloids are shown in the surface crack analysis. The arrows indicate positions of the respective colloids. Scale bar: 1 µm.
Figure 2C:
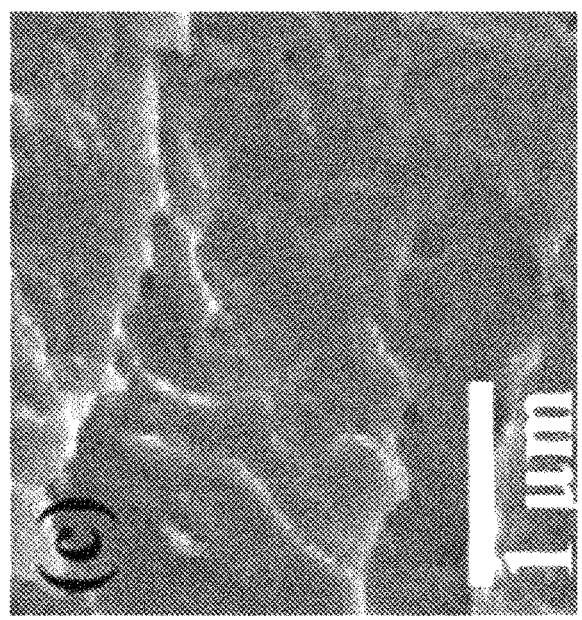
Figure 2F:
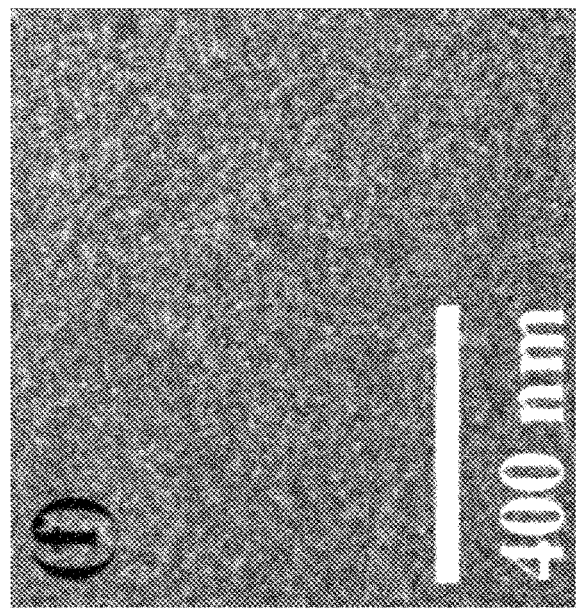
FIGS. 2F to 2H show transmission electron microscope (TEM) images of (f) colloids formed of HA and PVP at a ratio of 1:1 without NR and CAP, and colloids formed together with (g) NR or (h) CAP. Scale bar: 400 nm.
Figure 2E:
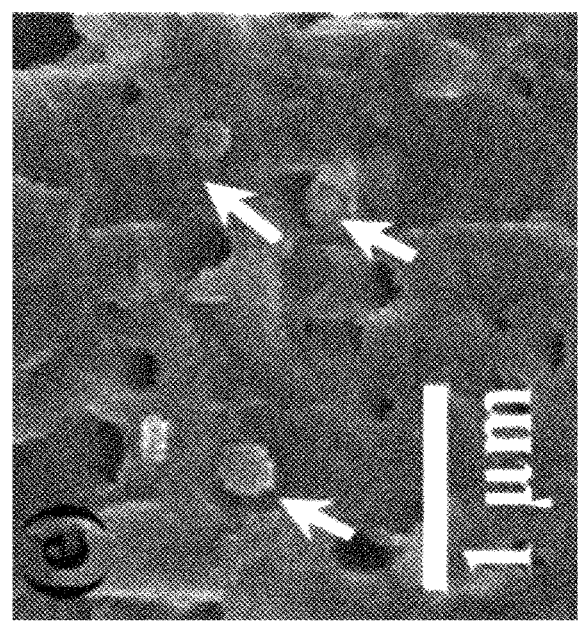
Figure 2H:
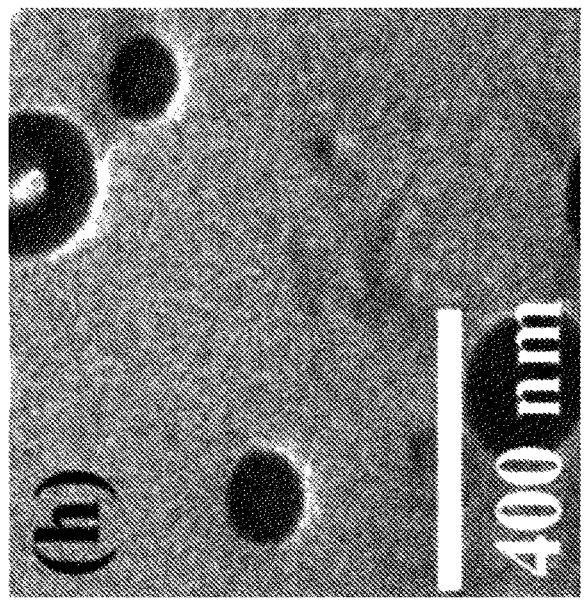
Figure 2G:
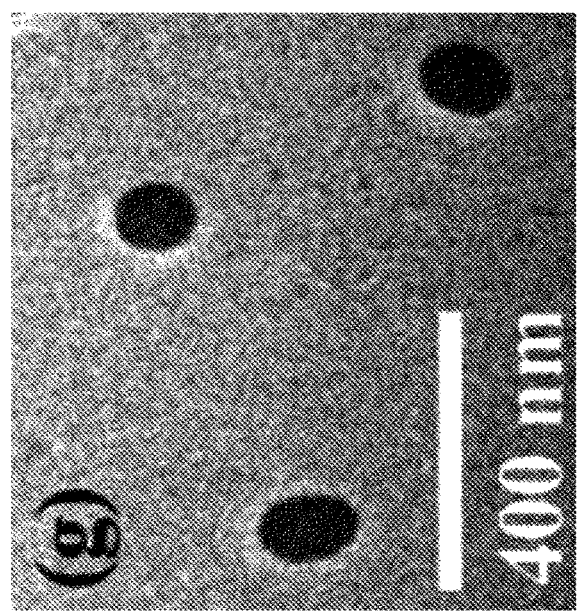
Figure 21:
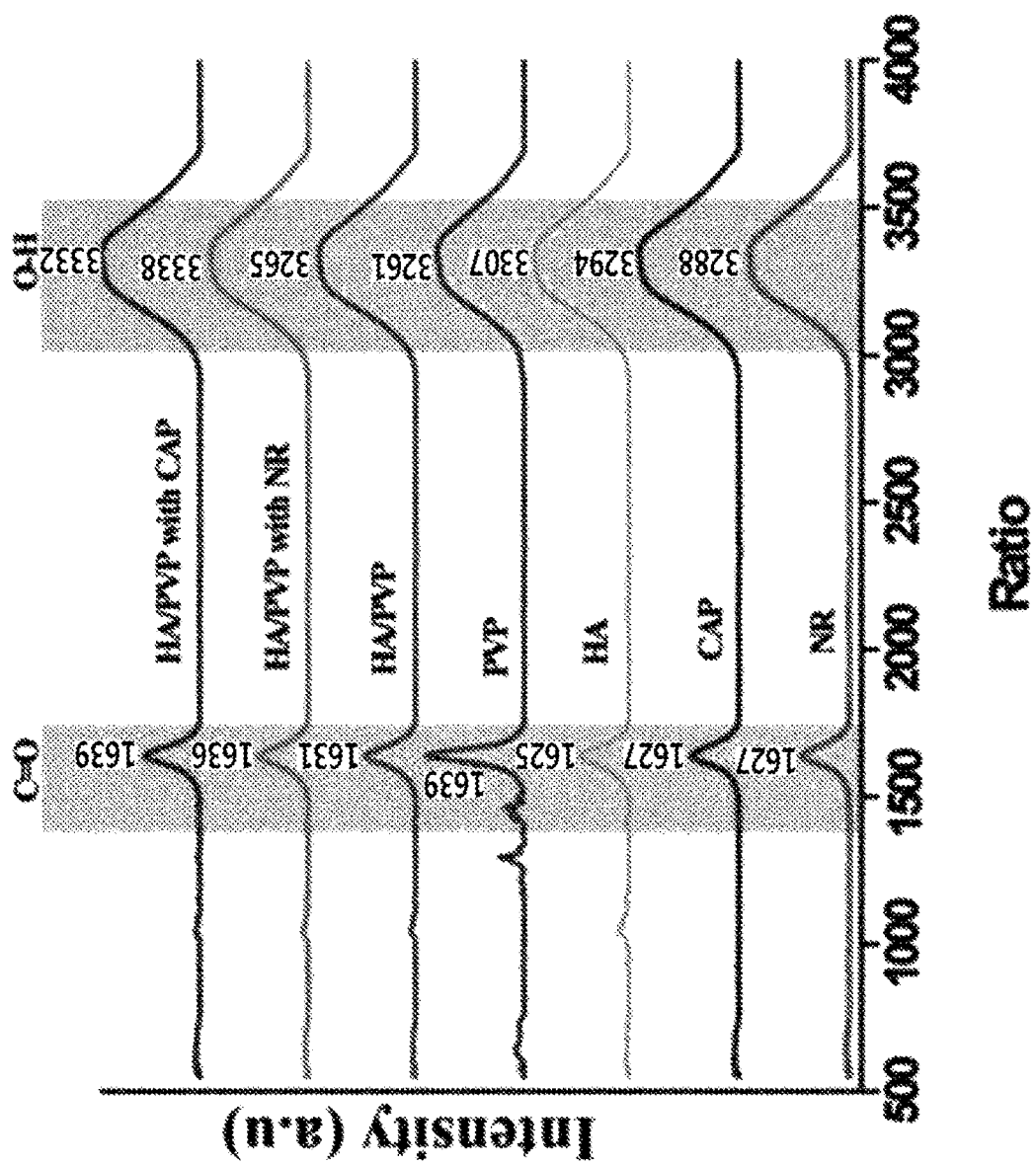

As proven on the scanning electron microscope (SEM) images (FIGS. 2C, 2D and 2E) and the transmission electron microscope (TEM) images (FIGS. 2F, 2G and 2H), the design of the SPS of the present invention leading to the formation of the colloidal structures was composed of hydrophobic (drug) and hydrophilic (HA) components. The SEM image showed that NR had a circular colloidal particle size of approximately 168±12 nm (indicated by arrows in the drawings), and CAP had a circular colloidal particle size of approximately 155±8 nm (FIG. 2E), and the same results come out in the particle size analysis data. Also, it was confirmed that such colloidal structures had a particle size of 161±32 nm in the case of NR and a particle size of 154±3 nm in the case of CAP, as viewed from the TEM images. The particle sizes measured by TEM were negligibly different from those of the particle size analysis data.

To evaluate a basic mechanism of the SPS leading to the formation of the colloidal structures, A Fourier transform infrared spectroscopy (FTIR) analysis (to analyze the interaction between the polymer and the drug, 14) was performed. When the polymer interacted with the drug via a certain chemical bond, certain peaks depending on atomic or molecular vibrations were observed (15). Apparently, an important determination factor in forming colloids through the SPS was the interaction between the lipophilic drug and the polymers such as HA and PVP (16). The previous studies showed that PVP was composed of heteroatoms and carbonyl groups in pyrrolidone rings. The pyrrolidone rings sufficiently reduced most of vibration modes, which led to a change in the frequency of carbonyl stretches which were very sensitive to hydrogen bonds which contribute to particle formation (17). Therefore, the spectra based on the effect of PVP in the SPS were observed. As shown in FIG. 2I, a blue block corresponded to the vibration of a carbonyl bond (a C=O stretch) generally appearing at 1,400 to 1,700 $cm^{-1}$, a yellow block corresponded to an alkane (a C—H stretch) appearing at 610 to 725 $cm^-$, and a pink block corresponded to a carboxylic acid (an O—H stretch) at 3,000 to 3,500 $cm^{-1}$. Even when the carbonyl vibrations were observed for NR; CAP; HA; PVP; HA:PVP; HA:PVP and NR; and HA:PVP and CAP, the vibrations had various positions and strengths. It was revealed that the C=O bond strength was high in the hydrophobic PVP (1,639 $cm^{-1}$) and the lipophilic drug (NR: 1,627 $cm^{-1}$; or CAP: 1,627 $cm^{-1}$). It was interesting that, in the combinations including the lipophilic drug, such as HA:PVP (1,631 $cm^{-1}$), HA:PVP with NR (1,635 $cm^{-1}$), and HA:PVP with CAP (1,639 $cm^{-1}$), a band shift around a PVP band stretch (1,639 $cm^{-1}$) having an effect of PVP forming an internal bond in the SPS was observed. However, the band shift was observed at 1,625 $cm^{-1}$ in a C=O bond band of HA. Also, the band was widely observed for hydrophobic PVP (1,407 to 1,749 $cm^{-1}$), NR (1,475 to 1,755 $cm^{-1}$), and CAP (1,485 to 1755 $cm^{-1}$). The band was narrowly observed for the combinations including PVP and the lipophilic drug, for example, HA:PVP and NR (1,494 to 1,755 $cm^{-1}$), and HA:PVP and CAP (1,490 to 1,755 $cm^{-1}$), indicating that the colloidal structures were formed in the SPS. A change in such a C=O wavenumber was caused when some electrons were transferred from a lone pair of electrons of oxygen in PVP to empty orbitals of NR and CAP. In this case, the change in the CO=wavenumber occurred when hydrogen atoms received the lone pair to form hydrogen bonds for particle formation which led to the formation of the colloidal structures in the SPS as described above, that is, particle formation.

Also, the ester bonds were widely observed at 3,288 $cm^{-1}$ for NR (2,939 to 3,705 $cm^{-1}$), at 3294 $cm^{-1}$ for CAP (2,937 to 3,697 $cm^{-1}$), and at 3,261 $cm^{-1}$ for PVP (2,916 to 3,691 $cm^{-1}$), but were somewhat weak, the results of which were proven to be narrower and weaker than those of HA (2,941 to 3,691 $cm^{-1}$) observed at 3,307 $cm^{-1}$. In comparison, a bond appearing at 3,265 $cm^{-1}$ for HA:PVP (2,943 to 3,691 $cm^{-1}$) was proven to narrower and weaker, indicating that HA had a probability of interacting with PVP via an ester bond. However, PVP including the lipophilic drug combination had a wide and stronger bond line as in HA:PVP and NR (2,945 to 3,695 $cm^{-1}$) at 3,338 $cm^{-1}$ and HA:PVP and CAP (2,933 to 3,695 $cm^{-1}$) at 3,332 $cm^{-1}$, indicating that the lipophilic drug easily formed an ester bond through PVP, compared to the ester bond formed through HA. Based on the results, the present inventors concluded that a carbonyl group of PVP and a hydroxyl group of the lipophilic drug interacted to form a hydrogen bond, thereby forming the colloids.

Figure 2J:
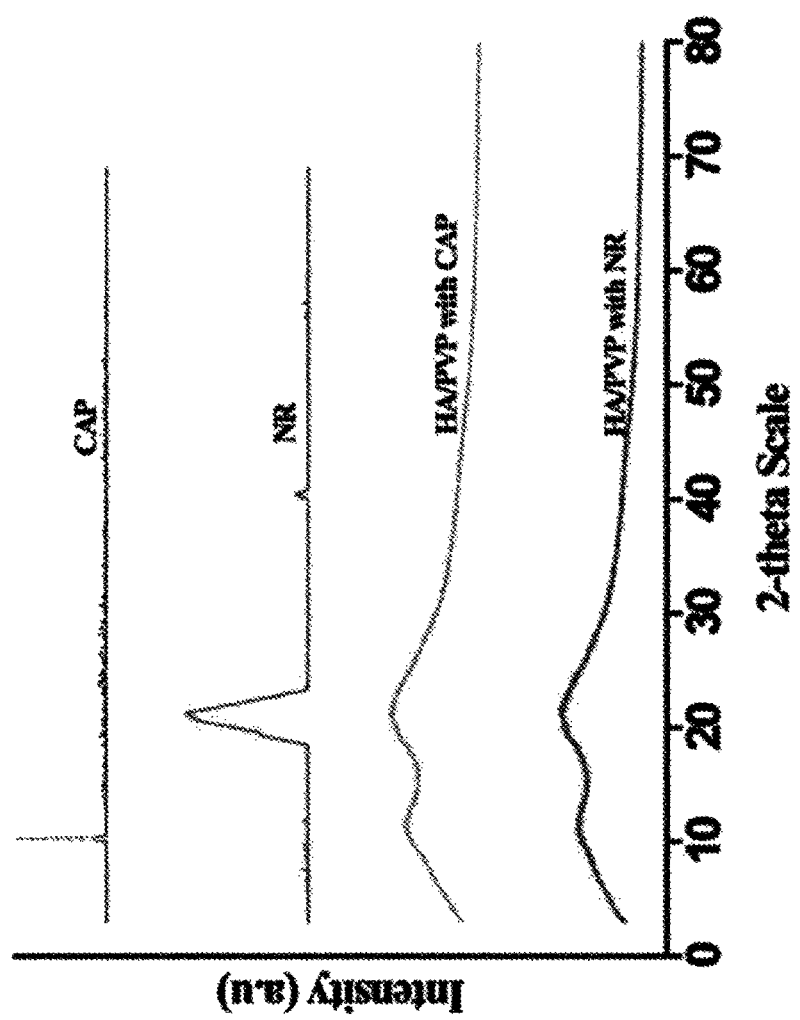
FIG. 2J shows X-ray diffraction (XRD) results obtained by examining amorphous forms of powders in the colloids. Scale bar: 1 mm.

It was possible to form nano-sized colloidal structures only when the microsized crystal powder-type lipophilic drug was phase-transitioned. It was important that the SPS was designed so that the properties of the polymers had an influence on a phase change of the powder-type lipophilic drug. Likewise, the above-described interaction was expected to prevent the crystallization by providing a binding site for stabilization of the drug in an amorphous state, which was referred to as a crystal positioning effect. A hydrogen bond between an amide carbonyl group of PVP and a hydrogen donor of the lipophilic drug was able to suppress the crystallization of the drug, and maintain an amorphous state (19). Also, it was expected that the crystalline drug was transformed into an amorphous state to improve solubility when the crystalline drug interacted with PVP. Therefore, the present inventors have performed X-ray diffraction analysis on two lipophilic drugs to determine the amorphization of the lipophilic drugs in the presence of PVP. Characteristic peaks were observed for NR and CAP when NR and CAP were in crude form. NR and CAP existed as crystal materials having diffraction peaks in which a diffraction angle 2θ was observed at 19.32 to 23.06 and 10.15 to 10.47 (FIG. 2J). However, a peak (a hump) of an amorphous phase appeared in the 1:1 combination of HA and PVP. The absence of the crystalline peak indicates the formation of the amorphous phase based on the previous studies (20). As described above, the three criteria for SPS design, that is, a decrease in particle size, colloid formation and amorphization, provide the means for proving that the powder-type lipophilic drug may be effectively combined with HA and PVP at the optimal ratio.

3. Evaluation of Cytotoxicity of SPS

Figure 3:
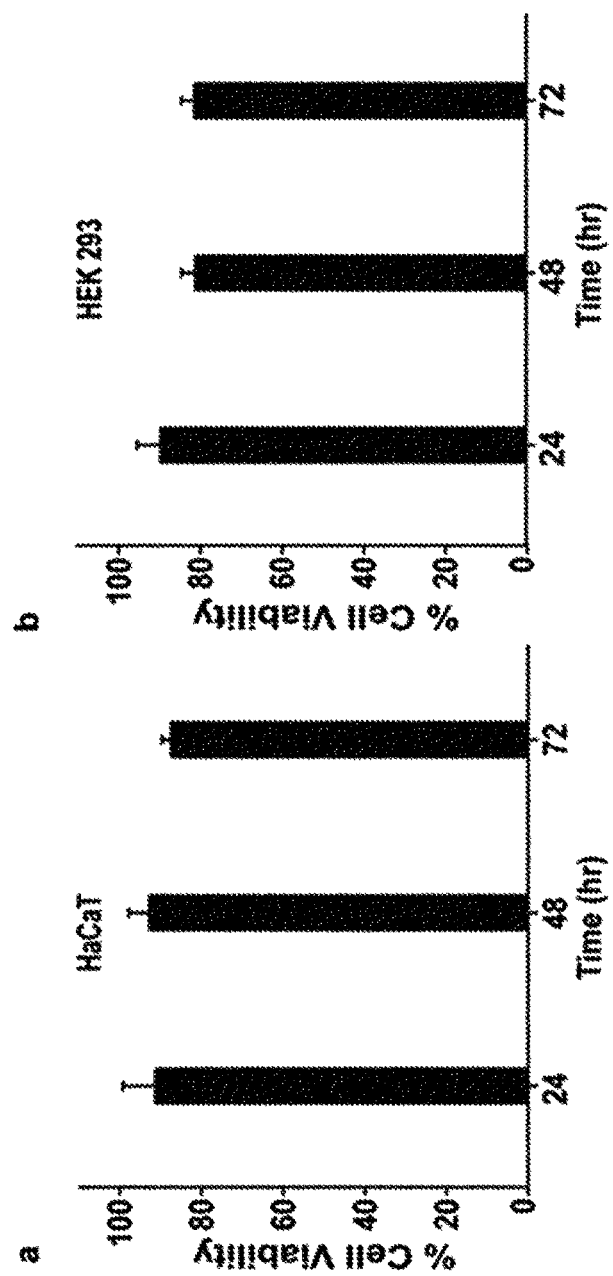
FIG. 3 shows cytotoxicity analysis results using an MTT assay for PVP used to fabricate CAP microneedles (CAP Mn). It can be seen that no cytotoxicity is observed in HaCaT (human adult low calcium high temperature) keratinocytes and HEK293 (human embryonic kidney) cells up to 72 hours after PVP administration (average±standard deviation, n=6, and p<0.05).

The present inventors have evaluated the cytotoxicity of the biodegradable polymer PVP used in the SPS for lipophilic drug delivery using an MTT assay (FIG. 3). A HaCaT cell line widely used to conduct research on polymers for transdermal delivery was used in a skin cell model, and a HEK293 cell line was used in a healthy human cell model. It could be seen that significant cytotoxicity was not observed for 72 hours and cell compatibility was maintained in both of the two experimental groups when an SPS extract was administered to each of the cell lines.

Figure 4A:
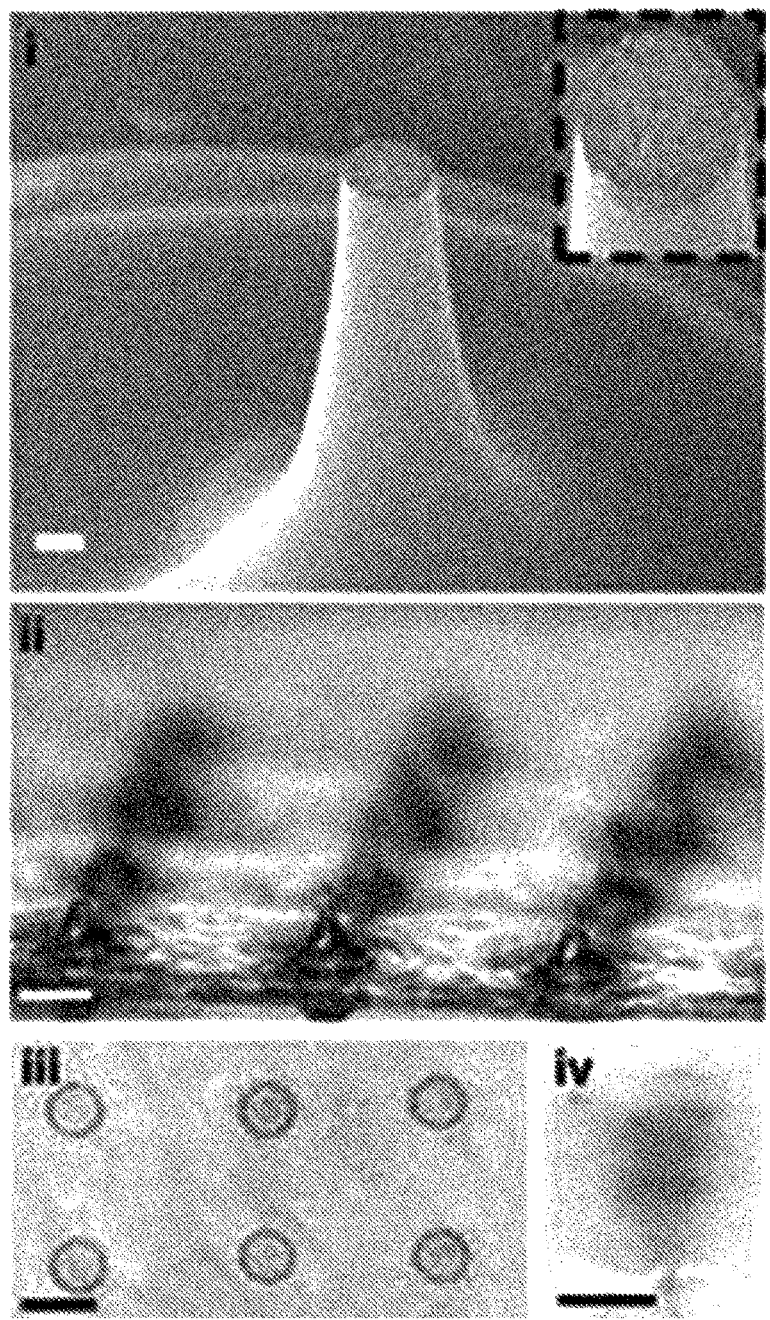
FIG. 4A shows SPS-based NR microneedles configured to induce amorphization and a decrease in the particle size of NR.

4. Fabrication of Microneedles Using SPS and In Vitro Analysis Through Franz Cell Analysis The present inventors have evaluated the SPS for successful lipophilic drug delivery. When the SPS was used, the effects such as a phase change, size reduction, and homogenization of the powder-type lipophilic drug were able to be obtained, as described above. However, when the powder-type lipophilic drug was topically applied directly to the skin, the powder-type lipophilic drug was not delivered (data not shown). Accordingly, a manner in which the powder-type lipophilic drug was able to overcome the skin barrier had to be sufficiently understood. In the previous studies, the biodegradable microneedles were fabricated to select the polymers for transdermal delivery. For the design of the SPS of the present invention, HA and PVP were able to be constructed into 3D microscaled devices, for example biodegradable microneedles, using drawing lithography based on the previous knowledge on the microneedles. A skin patch was manufactured using a technique developed to obtain a microneedle array, as shown in FIG. 4A (21). Therefore, the microneedles designed in the present invention were able to maintain the chemical integrity of the SPS and be provided with a SPS platform to deliver the powder-type lipophilic drug through the skin without any interruption.

Figure 4B:
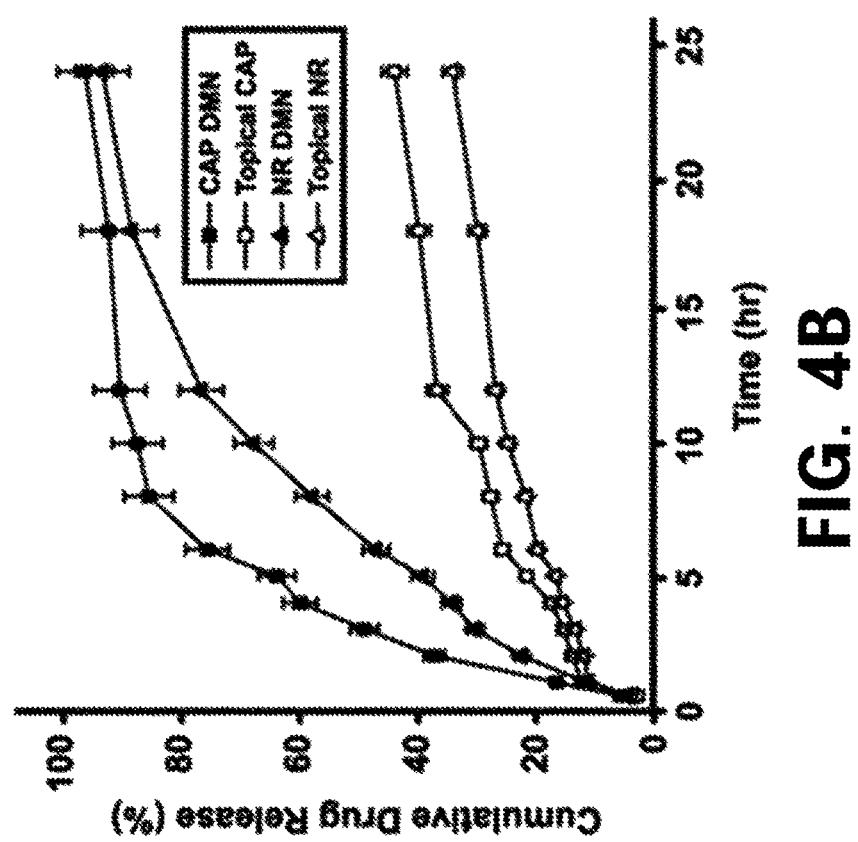
FIG. 4B shows a drug release profile when NR and CAP are topically applied to the skin of a dead pig through the NR and CAP microneedles (average±standard deviation, n=3).

To study the effective delivery of the powder-type lipophilic drug in the SPS through the microneedles, the release of NR and CAP from the microneedles was analyzed in vitro using Franz cell diffusion (FIG. 4B). NR was rapidly diffused within 30 minutes of application, and the concentration of the drug sharply increased within an hour, and then was maintained at a constant rate. On the other hand, CAP was diffused within an hour, and the drug was suddenly released for 2 hours, which indicated that the diffusion was dependent on the lipophilicity of the compound. NR having higher lipophilicity than CAP was more rapidly diffused. The drug was only released for several hours after application of the patch, the results of which were judged to be derived from a combined effect of the dissolution of the polymer and the diffusion of colloids through the skin layers. Although the release of CAP was observed to be 86% (n=3) after 12 hours of the application, the release of NR was observed to be 74% (n=3) after 8 hours of the application in the case of the microneedles loaded with NR. The release of the NR drug from a receptor steadily increased after an hour, and then slowly increased. In the case of CAP, the drug was released after 2 hours, and then slowly released for 8 hours. Then, the release of the drug gradually increased, indicating that the diffusion of such a lipophilic compound through the skin layers was passively adjusted. Since the compound was in a colloidal state, all the drugs were able to be diffused through the skin. This was confirmed by stirring a patch from Franz cells overnight in PBS including 20% ethanol.

Figure 4C:
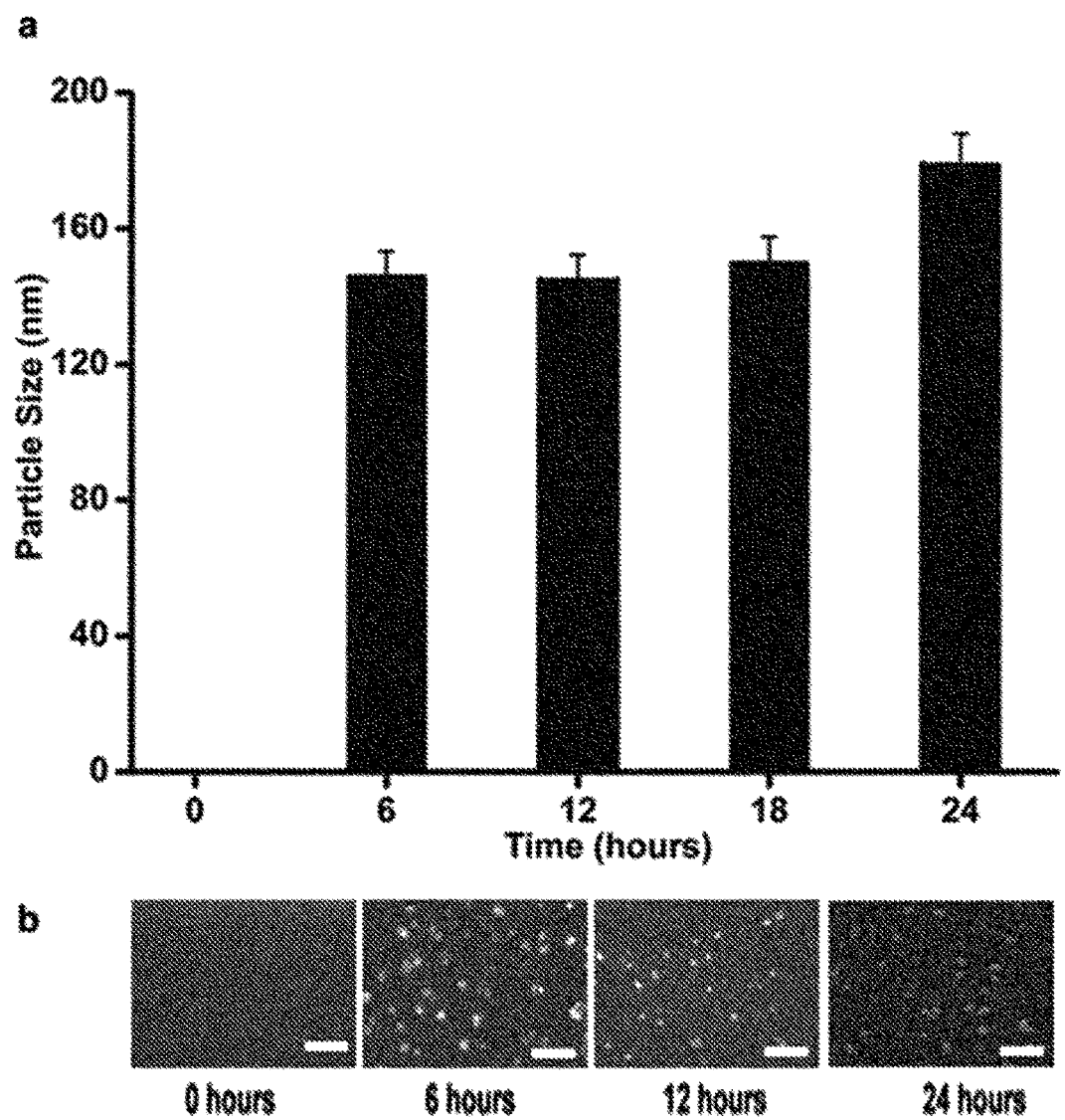
FIG. 4C shows the size analysis results of CAP particles released from the skin of the dead pig. It can be seen that the CAP particles having a similar size are steadily released for 24 hours (average±standard deviation, n=3). Scale bar: 1 μm.

Also, the size of CAP particles released during diffusion of the Franz cells in the skin of a dead pig (FIG. 4C) was measured. PBS solution samples were taken from the Franz cell receptor after 0, 6, 12, 24 hours of application of the CAP microneedles, and the particle sizes of the samples were measured through SEM image analysis. From the measured results, it was confirmed that the CAP particles having a predetermined size were released after 24 hours of application of the CAP microneedles.

5. In Vivo Analysis Using CAP Microneedles

To successful apply the microneedles as possible drug delivery systems, the present inventors have conducted research on an effect of the CAP microneedles for treatment of arthritis n DBA/1 mice (22). The previous studies showed that capsaicin inhibited the production of pre-inflammatory cytokines (for example, TNF-α, IL-1β and IL-6) through peroxisome proliferator-activated receptors (PPARs) (23). The therapeutic activity of CAP was evaluated by applying 0.75% CAP microneedles into or 0.75% topical CAP to the legs of 4-weeks-old type II collagen-induced arthritic (CIA) mice three times a week for 6 weeks.

Figure 5A:
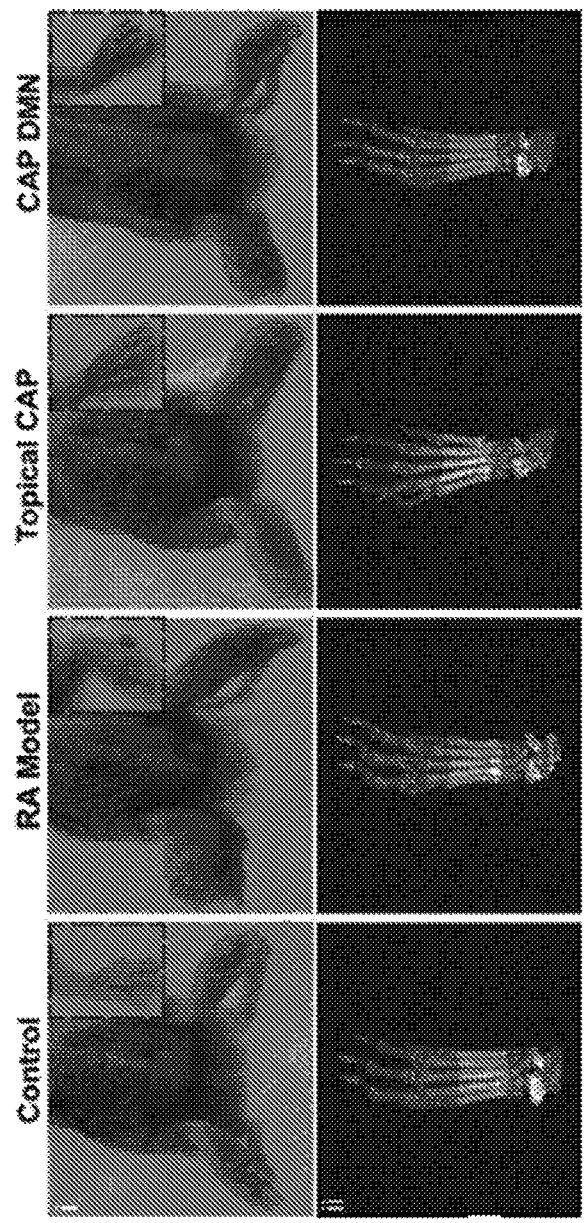
FIG. 5A shows digital camera images: As the control, type II collagen is not administered to normal DBA/1 mice, and the type II collagen is primarily administered in the $2^{nd}$ week, and secondarily administered in the $3^{rd}$ week in a rheumatoid arthritis (RA) model. A decrease in an edema in hind legs is observed in a topical CAP-treated group and a CAP Mn-treated group.
Figure 5B:
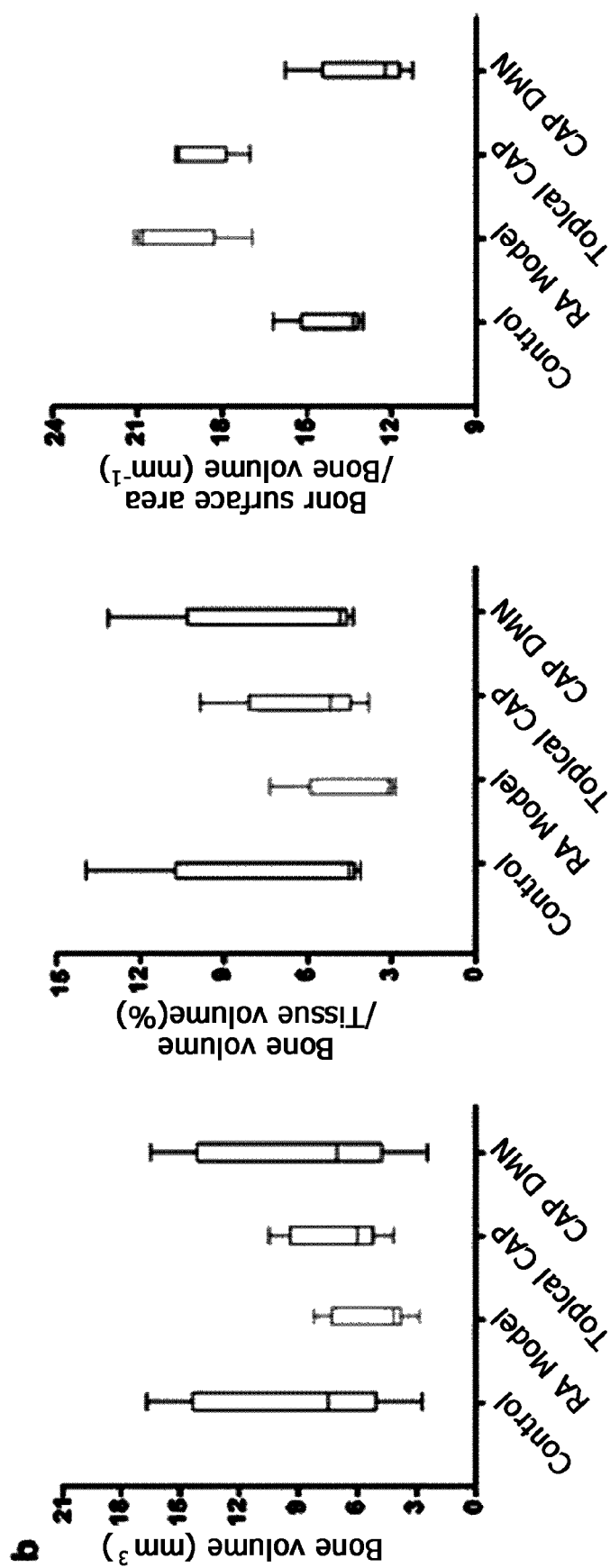
FIG. 5B shows results obtained by measuring a bone volume, a percentage of the bone volume, and a ratio of a bone surface area to the bone volume to determine levels of bone integrity and bone loss. A CAP microneedle-treated group was compared to an arthritis-free control. The BV and the bone volume/tissue volume (BV/TV) are measures of a level of bone preservation. As sown in FIG. 5B, it can be seen that the BV and BV/TV increase remarkably after treatment of the CAP microneedles (P<0.05).

The mice into which type II collagen was not administered were used as the control (n=8). It was confirmed that the induction of arthritis was observed with the naked eye on microscope images of an edema in the hind legs in an RA model (groups in which the CAP microneedle or topical CAP was not administered. However, the edema in the hind legs was clearly alleviated in the CAP microneedle (n=8)- and topical CAP (n=8)-treated groups (the upper panel of FIG. 5A). The alleviation of the edema in the hind legs through the CAP microneedle and topical CAP treatment was confirmed, and 3D micro-CT imaging was also performed to examine a change in bone during treatment of arthritis. As was expected, it was revealed that the immense destruction of bone was observed in the non-administered CIA groups, and the bone was intactly preserved in the CAP microneedle-treated groups (the lower panel of FIG. 5A): The bones in the CAP microneedle-treated CIA mice were compared to those of the control as shown in FIG. 5B. Also, the parameters for a level of bone preservation, that is, bone volume (BV) and bone volume/tissue volume (BV/TV) were measured after the treatment procedure.

Figure 5C:
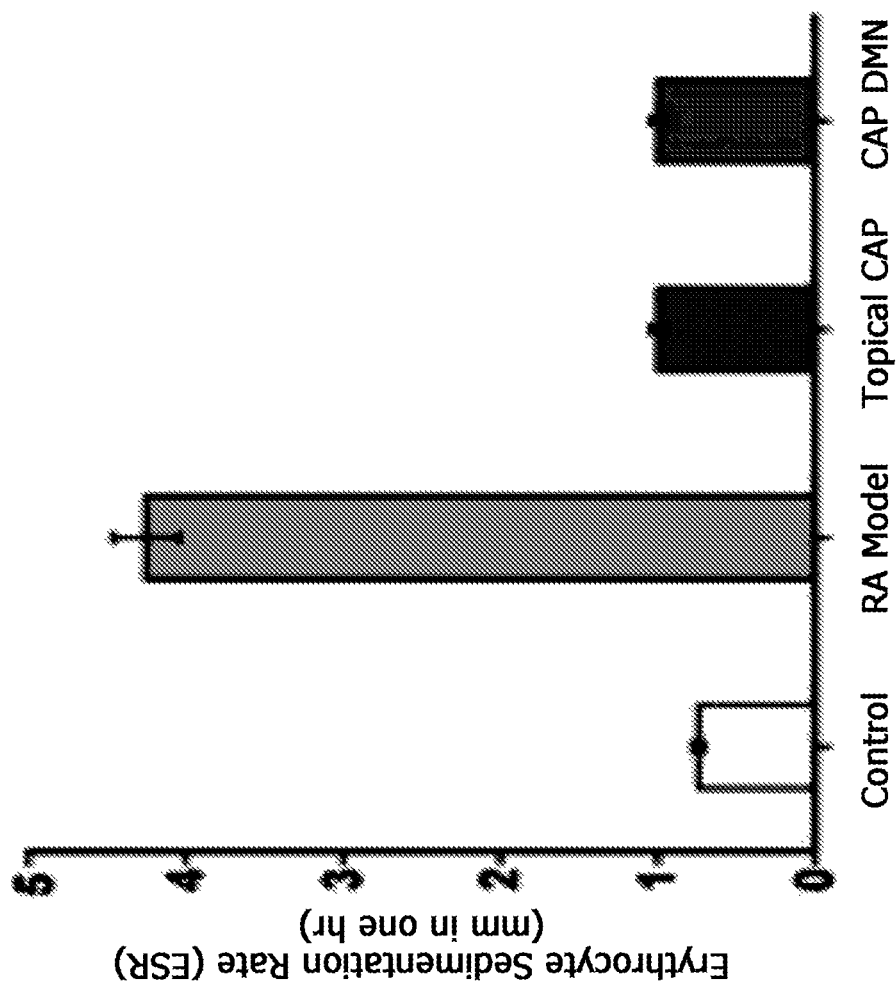
FIG. 5C shows results of evaluation of infections using an erythrocyte sedimentation rate (ESR). CAP Mn tends to settle at a reduced level, compared to the control and RA model.

The BV and BV/TB of the CAP microneedle-treated CIA mice significantly increased, compared to the control (p<0.05). Based on the imaging results, the present inventors have found that CAP was successfully delivered through the SPS system, and arthritis may be effectively alleviated by preserving the bone volume and integrity in the CIA mice. In the image analysis, the activity of CAP by which inflammations were alleviated at infected sites was finally measured by analyzing an erythrocyte sedimentation rate (ESR). The ESR is a clinical scale for evaluating the presence of rheumatoid arthritis (RA). Since the ESR represented a level of inflammation for RA, the ESR was compared to that of the arthritic mice having induced arthritis caused by CFA, as compared to the RA-free control. The increased ESR level observed in the arthritic mice significantly decreased by approximately 76.53% in the CAP microneedle-treated mice (P≤0.05, see FIG. 5C). Since RA was considered to be induced by a large number of pre-inflammatory molecules secreted by leukocytes including cytokines, the results showed that the CAP microneedles were effective for alleviating RA-induced inflammations. The main characteristic of RA was to continuously produce cytokines such as TNF-α, IL-1β, and IL-6 (24). Therefore, to determine an ability of the CAP microneedles to regulate the expression of inflammatory cytokines, the serum levels of the inflammatory cytokines such as TNF-α, IL-1β and IL-6 in the control, the RA model, and the CAP microneedle- and topical CAP-treated CIA mouse groups were quantitatively analyzed.

Figure 5D:
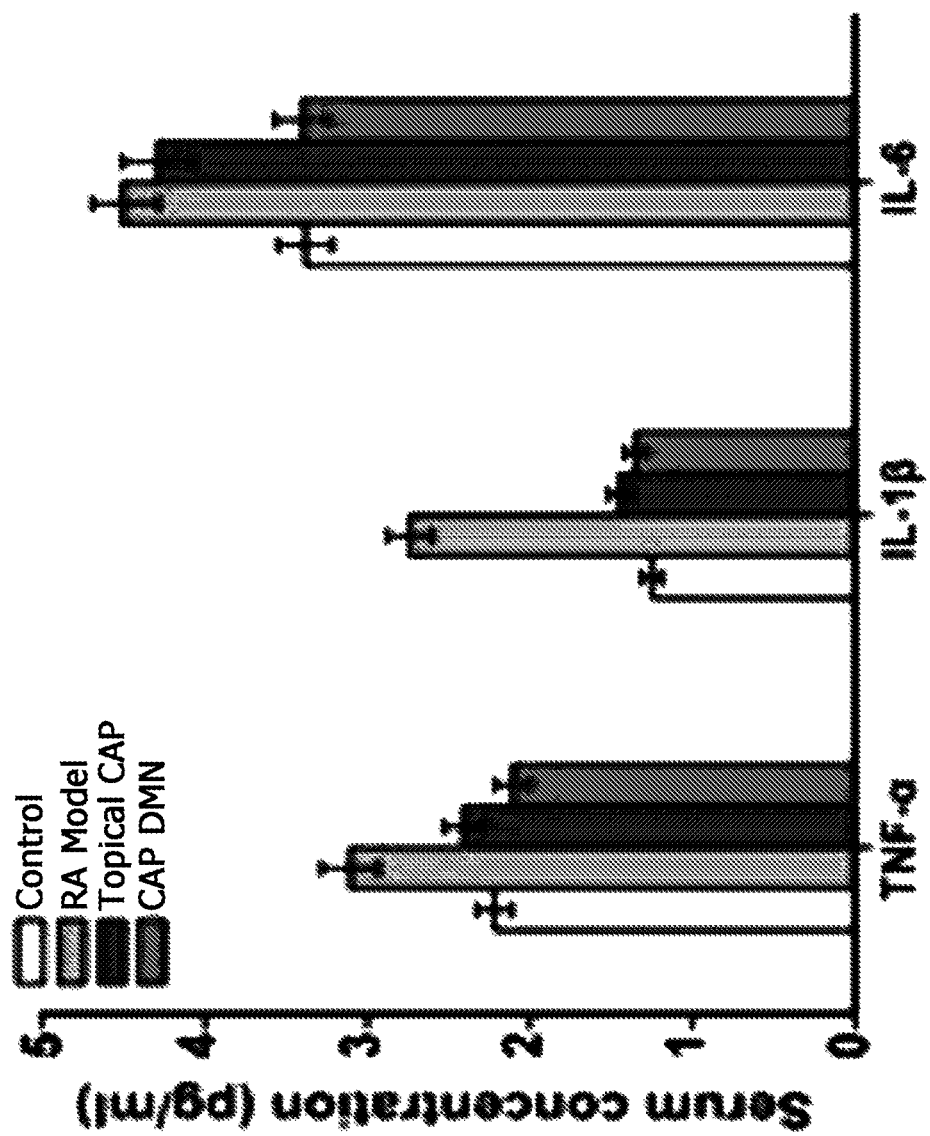
FIG. 5D show results obtained by measuring a level of cytokines in a serum exudate. Here, concentrations of TNF-α, IL-1β and IL-6 are indicated by pg/ml.
Figure 6:
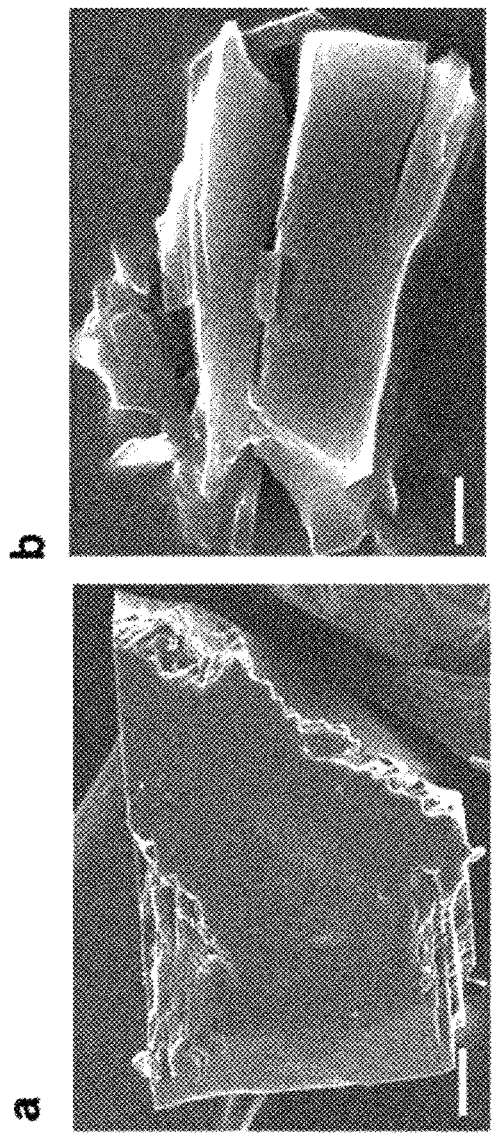
FIG. 6 shows microsized crystalline lipophilic drugs.
Figure 7:
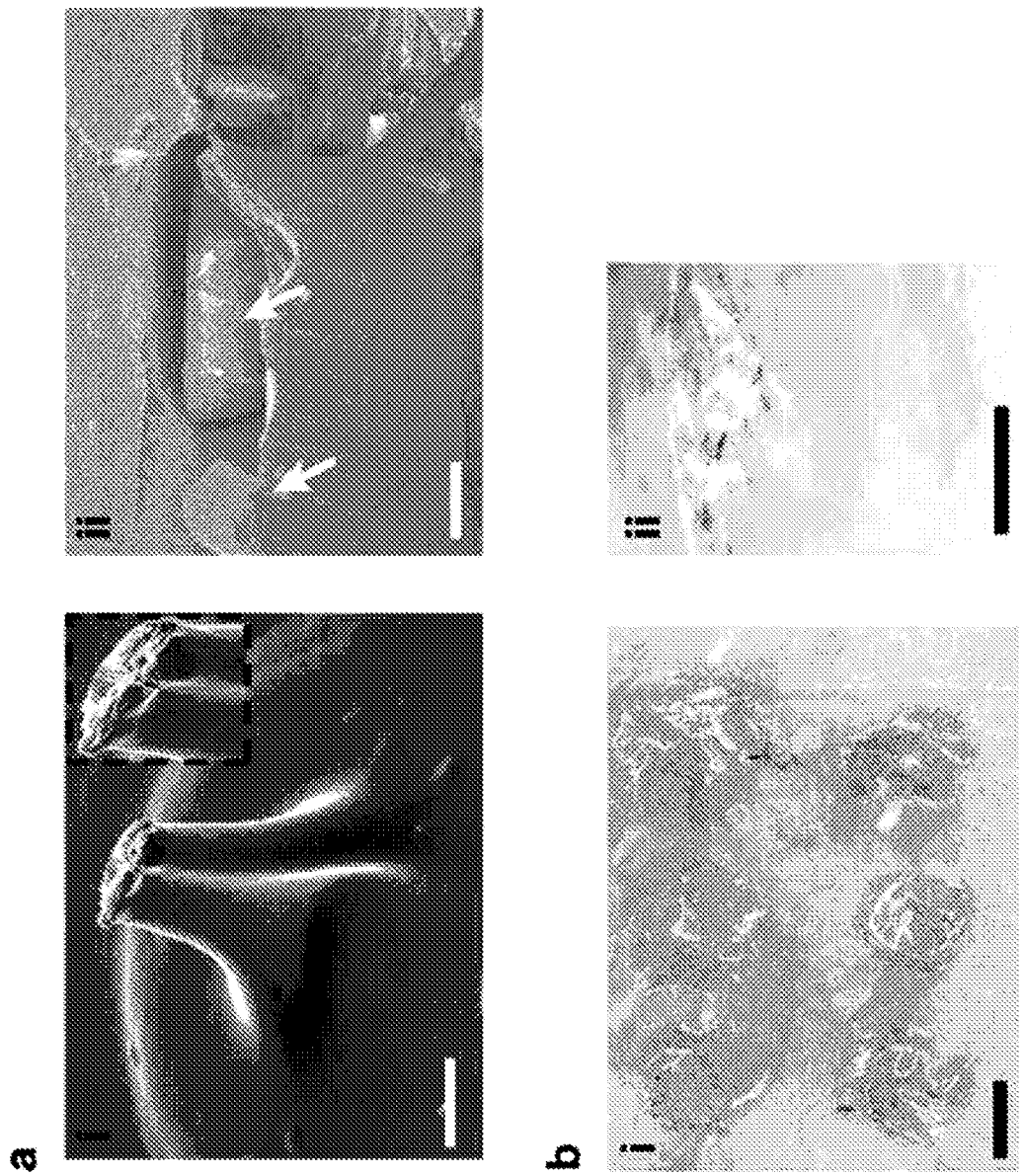
FIG. 7 shows results obtained by testing a microsized crystalline NR structure and permeation of the NR structure into the skin without using the SPS of the present invention.

As shown in FIG. 5D, all of the types of cytokines in the serum remarkably increased in the RA-induced mice. In the RA model, the serum levels of TNF-α and IL-6 increased onefold, and the serum level of IL-1β increased twofold, compared to the control. The TNF-α level decreased by approximately 32.18% in the CAP microneedle-treated group, the value of which was 10% higher than the topical CAP-treated group (22.51%). Also, the IL-1β level decreased by approximately 50% after the administration of CAP, the value of which was slightly higher, that is, approximately 3% higher than the topically treated group (47.11%). The IL-6 serum level after the application of the CAP microneedles was shown to be 24.54% in the RA model, the value of which was lower than that of the control. These results showed that the production of TNF-α, IL-1β and IL-6 in the leukocytes was readily regulated by the delivery of CAP through the SPS-based microneedles, compared to the topical application. Since CAP is an analogue ligand in PPARs positioned in epidermal nerve fibers (ENFs) derived from the outer layer of the skin, the microneedles were administered to directly expose the ENFs to CAP, inducing an elevated anti-inflammatory mechanism, compared to the topical application. The topical application was able to alleviate arthritis, but the delivery of the drugs caused the indirect exposure of the drug to the ENFs, and thus the drugs had a wide range of effects, indicating that the CAP microneedles were important in the development for treatment of RA.

A novel approach to administer the amorphous powder-type lipophilic drug in the SPS was proposed. Since the lipophilic drug was poorly soluble in water, the use of the drug in a soluble form was required upon drug administration. Therefore, since the drug was loaded in an amorphous form, the present inventors have proven the use of the microneedle system for the powder-type lipophilic drug to solve such solubility-related problems. The particle size of the colloids decreased due to the homogenization and the optimal ratio (1:1) of HA and PVP, the forms of the colloidal structures including the lipophilic drug as such particles, for example, an amorphous powder form, were confirmed through SEM and TEM. It was confirmed that the formation of the colloidal structure through the interaction between the lipophilic drug and HA and PVP was due to the dissolution of the drug in the presence of PVP. A mechanism based on stabilization and solubility was described by FTIR analysis.

As a result, the smart polymer system according to one exemplary embodiment of the present invention has a probability of fabricating the "biodegradable microneedles loadable with the lipophilic drug," and the microneedles loaded with capsaicin using the smart polymer system will be an effective tool to treat rheumatoid arthritis. Also, since the smart polymer system of the present invention in which a solvent is not used enables safe and efficient lipophilic drug delivery, such a system will be a novel breakthrough in delivery of thousands of lipophilic drugs which do not include a proper solvent, show low bioavailability, or have a large molecular weight.

It will be apparent to those skilled in the art that various modifications can be made to the above-described exemplary embodiments of the present invention without departing from the scope of the invention. Thus, it is intended that the present invention covers all such modifications provided they come within the scope of the appended claims and their equivalents.

REFERENCES

1. Box K J, & Comer, J. E. A. "Using Measured pKa, Log P and Solubility to Investigate Supersaturation and Predict BCS Class." Current Drug Metabolism 2008, 9(9): 869-878.
2. Leeson P D, Springthorpe B. The influence of drug-like concepts on decision-making in medicinal chemistry. Nature Reviews Drug Discovery 2007, 6(11): 881-890.
3. Wadhwa J, Nair A, Kumria R. Emulsion forming drug delivery system for lipophilic drugs. Acta Pol Pharm 2012, 69(2): 179-191.
4. Rautio J, Kumpulainen H, Heimbach T, Oliyai R, Oh D, Järvinen T, et al. Prodrugs: design and clinical applications. Nature Reviews Drug Discovery 2008, 7(3): 255-270.
5. Dick F. Solvent neurotoxicity. Occupational and environmental medicine 2006, 63(3): 221-226.
6. Lipinski C A. Drug-like properties and the causes of poor solubility and poor permeability. Journal of pharmacological and toxicological methods 2000, 44(1): 235-249.
7. Funke A P, Günther C, Müller R H, Lipp R. In-vitro release and transdermal fluxes of a highly lipophilic drug and of enhancers from matrix TDS. Journal of controlled release 2002, 82(1): 63-70.
8. Wang J D, Douville N J, Takayama S, ElSayed M. Quantitative analysis of molecular absorption into PDMS microfluidic channels. Annals of biomedical engineering 2012, 40(9): 1862-1873.
9. Lazar J, Braun D C, Toth A, Wang Y, Pearce L V, Pavlyukovets V A, et al. Kinetics of penetration influence the apparent potency of vanilloids on TRPV 1. Molecular pharmacology 2006, 69(4): 1166-1173.
10. Ito Y, Yoshimura M, Tanaka T, Takada K. Effect of lipophilicity on the bioavailability of drugs after percutaneous administration by dissolving microneedles. Journal of pharmaceutical sciences 2012, 101(3): 1145-1156.
11. Singhavi D J, Khan S, Yeole P G. Improvement of dissolution behavior of poorly water soluble drugs by biodegradable polymeric submicron carriers containing sparingly methylated β-cyclodextrin. Journal of Materials Science: Materials in Medicine 2013, 24(4): 941-949.
12. Kim M, Yang H, Kim H, Jung H. Novel cosmetic patches for wrinkle improvement: retinyl retinoate- and ascorbic acid-loaded dissolving microneedles. International Journal of Cosmetic Science 2014, 36(3): 207-212.
13. Liu J, Hoffmann H. Hydrogels in aqueous phases of polyvinylalcohol (PVA), surfactants and clay minerals. Colloid and Polymer Science 2004, 283(1): 24-32.
14. Manju S, Sreenivasan K. Conjugation of curcumin onto hyaluronic acid enhances its aqueous solubility and stability. Journal of colloid and interface science 2011, 359(1): 318-325.
15. Sawant P D, Luu D, Ye R, Buchta R. Drug release from hydroethanolic gels. Effect of drug's lipophilicity (log P), polymer-drug interactions and solvent lipophilicity. International journal of pharmaceutics 2010, 396(1): 45-52.
16. Chadha R K V, Kumar A. Analytical techniques used to characterize drug-polyvinylpyrrolidone systems in solid and liquid states—An overiview. Journal of Scientific & Industrial Research 2006, 65: 459-469.
17. Tu W X Z X, Liu H F. Study on the interaction between polyvinylpyrrolidone and platinum metals during the formation of the colloidal metal nanoparticles. Polymer Science 2008, 26(1): 23-29.
18. Schulz M, Fussnegger B, Bodmeier R. Influence of adsorbents in transdermal matrix patches on the release and the physical state of ethinyl estradiol and levonorgestrel. European Journal of Pharmaceutics and Biopharmaceutics 2011, 77(2): 240-248.
19. Ma X T J, Chiang C M. Control of drug crystallization in transdermal matrix system. International journal of pharmaceutics 1996, 142(1): 115-119.
20. Tekade A R G S. Investigation on Physical-Mechanical Properties of Natural Polymer Films. International Journal of Pharmtech Research 2010, 2(1): 106-112.
21. Kim J D, Kim M, Yang H, Lee K, Jung H. Droplet-born air blowing: novel dissolving microneedle fabrication. Journal of Controlled Release 2013, 170(3): 430-436.
22. Brand D D, Latham K A, Rosloniec E F. Collagen-induced arthritis. Nature protocols 2007, 2(5): 1269-1275.
23. Park J-Y, Kawada T, Han I-S, Kim B-S, Goto T, Takahashi N, et al. Capsaicin inhibits the production of tumor necrosis factor α by LPS-stimulated murine macrophages, RAW 264.7: a PPARγ ligand-like action as a novel mechanism. FEBS letters 2004, 572(1): 266-270.
24. Whitehouse M. Tumour necrosis factor alpha inhibitors for the treatment of adult rheumatoid arthritis. Biochem Biophys Res Commun 1988, 155: 1230-1236.

The invention claimed is:

1. A viscous composition for transdermal drug delivery, comprising colloidal particles formed of a combination of a lipophilic drug and a biodegradable polymer comprising polyvinyl pyrrolidone (PVP) and hyaluronic acid (HA), wherein the weight ratio of PVP to HA ranges from 20:1 to 1:20, wherein the lipophilic drug is bound to the polyvinyl pyrrolidone (PVP), and wherein the lipophilic drug is homogenized in the biodegradable polymer without a solubilizing solvent for the lipophilic drug.

2. The viscous composition of claim 1, wherein the lipophilic drug from which the colloidal particles are formed is in powder form.

3. The viscous composition of claim 1, wherein the lipophilic drug from which the colloidal particles are formed is crystalline, semicrystalline, or amorphous.

4. The viscous composition of claim 1, wherein the biodegradable polymer comprises polyvinyl pyrrolidone (PVP) and hyaluronic acid (HA) at a weight ratio ranging from 5:1 to 1:5.

5. The viscous composition of claim 1, wherein the colloidal particles have a core-shell structure in which the biodegradable polymer surrounds the lipophilic drug.

6. The viscous composition of claim 1, wherein the colloidal particles have a decreased colloidal particle size since the lipophilic drug is phase-transitioned due to a chemical bond or chemical interaction between the lipophilic drug and the biodegradable polymer, relative to the particle size of colloidal particles formed of a combination of the lipophilic drug and a biodegradable polymer that consists of a single homopolymer.

7. A method of preparing a viscous composition for transdermal drug delivery, comprising: homogenizing a lipophilic drug in a biodegradable polymer comprising polyvinyl pyrrolidone (PVP) and hyaluronic acid (HA) without a solubilizing solvent for the lipophilic drug, and wherein PVP and HA are present in a weight ratio ranging from 20:1 to 1:20.

8. The method of claim 7, wherein the step of homogenizing is performed by a method that comprises simple dispersion, mechanical dispersion, ultrasonic dispersion, or a combination thereof.

9. A microstructure device comprising:
a substrate, and
microstructure formed on the substrate, wherein each of the microstructures comprises colloidal particles formed of a combination of a lipophilic drug and a biodegradable polymer comprising polyvinyl pyrrolidone (PVP) and hyaluronic acid (HA), wherein the weight ratio of PVP to HA ranges from 20:1 to 1:20, wherein the lipophilic drug is bound to the polyvinyl pyrrolidone (PVP), and wherein the lipophilic drug is homogenized in the biodegradable polymer without a solubilizing solvent for the lipophilic drug.

10. The microstructure device of claim 9, wherein the microstructures are microneedles, microblades, microknives, microfibers, microspikes, microprobes, microbarbs, microarrays, or microelectrodes.

* * * * *

UNITED STATES PATENT AND TRADEMARK OFFICE
CERTIFICATE OF CORRECTION

| | | |
|---|---|---|
| PATENT NO. | : 10,537,518 B2 | Page 1 of 1 |
| APPLICATION NO. | : 15/105465 | |
| DATED | : January 21, 2020 | |
| INVENTOR(S) | : Hyung Il Jung and Dangol Manita | |

It is certified that error appears in the above-identified patent and that said Letters Patent is hereby corrected as shown below:

On the Title Page

Item [56], "JP 10-0793615 B1" should read -- KR 10-0793615 B1 --.

Signed and Sealed this
Twenty-fourth Day of March, 2020

Andrei Iancu
*Director of the United States Patent and Trademark Office*